(12) United States Patent
Hayter et al.

(10) Patent No.: US 9,398,872 B2
(45) Date of Patent: *Jul. 26, 2016

(54) METHOD AND APPARATUS FOR PROVIDING ANALYTE SENSOR CALIBRATION

(71) Applicant: Abbott Diabetes Care Inc., Alameda, CA (US)

(72) Inventors: Gary Alan Hayter, Oakland, CA (US); Geoffrey V. McGarraugh, Bodega Bay, CA (US); Andrew H. Naegeli, Walnut Creek, CA (US); John Charles Mazza, Long Beach, CA (US); Benjamin Jay Feldman, Berkeley, CA (US); Wesley Scott Harper, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/472,341

(22) Filed: Aug. 28, 2014

(65) Prior Publication Data

US 2014/0372065 A1 Dec. 18, 2014

Related U.S. Application Data

(63) Continuation of application No. 11/831,881, filed on Jul. 31, 2007, now Pat. No. 8,834,366.

(51) Int. Cl.
| | | |
|---|---|---|
| *A61B 5/00* | (2006.01) |
| *A61B 5/05* | (2006.01) |
| *A61B 5/1495* | (2006.01) |
| *A61B 5/01* | (2006.01) |
| *A61B 5/145* | (2006.01) |
| *G06F 19/00* | (2011.01) |

(52) U.S. Cl.
CPC .................. *A61B 5/1495* (2013.01); *A61B 5/01* (2013.01); *A61B 5/1451* (2013.01); *A61B 5/14532* (2013.01); *G06F 19/3412* (2013.01); *A61B 2560/0252* (2013.01)

(58) Field of Classification Search
USPC ........................................................ 600/365
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |

(Continued)

FOREIGN PATENT DOCUMENTS

| | | |
|---|---|---|
| CA | 2143172 | 7/2005 |
| DE | 4401400 | 7/1995 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Navin Natnithithadha
*Assistant Examiner* — Michael R Bloch
(74) *Attorney, Agent, or Firm* — One LLP

(57) ABSTRACT

Methods and apparatus for providing data processing and control for use in verifying the stability of sensor sensitivity of an analyte sensor.

21 Claims, 18 Drawing Sheets

(56) References Cited

U.S. PATENT DOCUMENTS

| | | |
|---|---|---|
| 3,960,497 A | 6/1976 | Acord et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |

(56) References Cited

U.S. PATENT DOCUMENTS

| | | | |
|---|---|---|---|
| 6,130,623 | A | 10/2000 | MacLellan et al. |
| 6,134,461 | A | 10/2000 | Say et al. |
| 6,143,164 | A | 11/2000 | Heller et al. |
| 6,144,871 | A | 11/2000 | Saito et al. |
| 6,159,147 | A | 12/2000 | Lichter et al. |
| 6,162,611 | A | 12/2000 | Heller et al. |
| 6,175,752 | B1 | 1/2001 | Say et al. |
| 6,200,265 | B1 | 3/2001 | Walsh et al. |
| 6,212,416 | B1 | 4/2001 | Ward et al. |
| 6,219,574 | B1 | 4/2001 | Cormier et al. |
| 6,233,471 | B1 | 5/2001 | Berner et al. |
| 6,248,067 | B1 | 6/2001 | Causey, III et al. |
| 6,254,586 | B1 | 7/2001 | Mann et al. |
| 6,270,455 | B1 | 8/2001 | Brown |
| 6,275,717 | B1 | 8/2001 | Gross et al. |
| 6,283,761 | B1 | 9/2001 | Joao |
| 6,284,478 | B1 | 9/2001 | Heller et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,299,347 | B1 | 10/2001 | Pompei |
| 6,306,104 | B1 | 10/2001 | Cunningham et al. |
| 6,309,884 | B1 | 10/2001 | Cooper et al. |
| 6,314,317 | B1 | 11/2001 | Willis |
| 6,329,161 | B1 | 12/2001 | Heller et al. |
| 6,348,640 | B1 | 2/2002 | Navot et al. |
| 6,359,270 | B1 | 3/2002 | Bridson |
| 6,359,444 | B1 | 3/2002 | Grimes |
| 6,360,888 | B1 | 3/2002 | McIvor et al. |
| 6,366,794 | B1 | 4/2002 | Moussy et al. |
| 6,377,828 | B1 | 4/2002 | Chaiken et al. |
| 6,379,301 | B1 | 4/2002 | Worthington et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,413,393 | B1 | 7/2002 | Van Antwerp et al. |
| 6,416,471 | B1 | 7/2002 | Kumar et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,440,068 | B1 | 8/2002 | Brown et al. |
| 6,471,689 | B1 | 10/2002 | Joseph et al. |
| 6,478,736 | B1 | 11/2002 | Mault |
| 6,484,046 | B1 | 11/2002 | Say et al. |
| 6,493,069 | B1 | 12/2002 | Nagashimada et al. |
| 6,496,729 | B2 | 12/2002 | Thompson |
| 6,497,655 | B1 | 12/2002 | Linberg et al. |
| 6,498,043 | B1 | 12/2002 | Schulman et al. |
| 6,514,718 | B2 | 2/2003 | Heller et al. |
| 6,520,326 | B2 | 2/2003 | McIvor et al. |
| 6,544,212 | B2 | 4/2003 | Galley et al. |
| 6,546,268 | B1 | 4/2003 | Ishikawa et al. |
| 6,549,796 | B2 | 4/2003 | Sohrab |
| 6,551,494 | B1 | 4/2003 | Feldman et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Plante et al. |
| 6,571,128 | B2 | 5/2003 | Lebel et al. |
| 6,572,545 | B2 | 6/2003 | Knobbe et al. |
| 6,574,490 | B2 | 6/2003 | Abbink et al. |
| 6,574,510 | B2 | 6/2003 | Von Arx et al. |
| 6,576,101 | B1 | 6/2003 | Heller et al. |
| 6,577,899 | B2 | 6/2003 | Lebel et al. |
| 6,579,231 | B1 | 6/2003 | Phipps |
| 6,579,690 | B1 | 6/2003 | Bonnecaze et al. |
| 6,585,644 | B2 | 7/2003 | Lebel et al. |
| 6,591,125 | B1 | 7/2003 | Buse et al. |
| 6,595,919 | B2 | 7/2003 | Berner et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,610,012 | B2 | 8/2003 | Mault |
| 6,633,772 | B2 | 10/2003 | Ford et al. |
| 6,635,014 | B2 | 10/2003 | Starkweather et al. |
| 6,635,167 | B1 | 10/2003 | Richards et al. |
| 6,641,533 | B2 | 11/2003 | Causey, III et al. |
| 6,648,821 | B2 | 11/2003 | Lebel et al. |
| 6,654,625 | B1 | 11/2003 | Say et al. |
| 6,656,114 | B1 | 12/2003 | Poulsen et al. |
| 6,658,396 | B1 | 12/2003 | Tang et al. |
| 6,659,948 | B2 | 12/2003 | Lebel et al. |
| 6,668,196 | B1 | 12/2003 | Villegas et al. |
| 6,675,030 | B2 | 1/2004 | Ciurczak et al. |
| 6,676,816 | B2 | 1/2004 | Mao et al. |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,702,857 | B2 | 3/2004 | Brauker et al. |
| 6,730,025 | B1 | 5/2004 | Platt |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,740,075 | B2 | 5/2004 | Lebel et al. |
| 6,740,518 | B1 | 5/2004 | Duong et al. |
| 6,741,877 | B1 | 5/2004 | Shults et al. |
| 6,746,582 | B2 | 6/2004 | Heller et al. |
| 6,758,810 | B2 | 7/2004 | Lebel et al. |
| 6,770,030 | B1 | 8/2004 | Schaupp et al. |
| 6,789,195 | B1 | 9/2004 | Prihoda et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,850,790 | B2 | 2/2005 | Berner et al. |
| 6,862,465 | B2 | 3/2005 | Shults et al. |
| 6,865,407 | B2 | 3/2005 | Kimball et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,882,940 | B2 | 4/2005 | Potts et al. |
| 6,892,085 | B2 | 5/2005 | McIvor et al. |
| 6,895,263 | B2 | 5/2005 | Shin et al. |
| 6,895,265 | B2 | 5/2005 | Silver |
| 6,923,763 | B1 | 8/2005 | Kovatchev et al. |
| 6,923,764 | B2 | 8/2005 | Aceti et al. |
| 6,931,327 | B2 | 8/2005 | Goode, Jr. et al. |
| 6,932,894 | B2 | 8/2005 | Mao et al. |
| 6,936,006 | B2 | 8/2005 | Sabra |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman, IV et al. |
| 6,958,705 | B2 | 10/2005 | Lebel et al. |
| 6,968,294 | B2 | 11/2005 | Gutta et al. |
| 6,971,274 | B2 | 12/2005 | Olin |
| 6,974,437 | B2 | 12/2005 | Lebel et al. |
| 6,983,176 | B2 | 1/2006 | Gardner et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,009,511 | B2 | 3/2006 | Mazar et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |

(56) References Cited

U.S. PATENT DOCUMENTS

| | | |
|---|---|---|
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,999,674 B2 | 8/2011 | Kamen |
| 8,010,174 B2 | 8/2011 | Goode et al. |
| 8,010,256 B2 | 8/2011 | Oowada |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |

(56) References Cited

U.S. PATENT DOCUMENTS

| | | |
|---|---|---|
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,160,900 B2 | 4/2012 | Taub et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 8,478,557 B2 | 7/2013 | Hayter et al. |
| 8,597,570 B2 | 12/2013 | Terashima et al. |
| 2001/0037366 A1 | 11/2001 | Webb et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1* | 6/2005 | Kamath et al. ................ 600/347 |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |

(56) References Cited

U.S. PATENT DOCUMENTS

| | | |
|---|---|---|
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zivitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |

(56) References Cited

U.S. PATENT DOCUMENTS

| | | |
|---|---|---|
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter et al. |
| 2008/0288204 A1 | 11/2008 | Hayter |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |

(56) References Cited

U.S. PATENT DOCUMENTS

| | | |
|---|---|---|
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213080 A1 | 8/2010 | Celentano et al. |
| 2010/0240975 A1 | 9/2010 | Goode et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0312176 A1 | 12/2010 | Lauer et al. |
| 2010/0313105 A1 | 12/2010 | Nekoomaram et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0081726 A1 | 4/2011 | Berman et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0245447 A1 | 9/2012 | Karan et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 0724859 | 8/1996 |
| EP | 0678308 | 5/2000 |
| EP | 1048264 | 11/2000 |
| EP | 1292218 | 3/2003 |
| EP | 1077634 | 7/2003 |
| EP | 1568309 | 8/2005 |
| EP | 1666091 | 6/2006 |
| EP | 1703697 | 9/2006 |
| EP | 1704893 | 9/2006 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |

(56) References Cited

FOREIGN PATENT DOCUMENTS

| | | |
|---|---|---|
| EP | 1448489 | 8/2010 |
| EP | 1971396 | 8/2010 |
| EP | 2201969 | 3/2011 |
| EP | 2153382 | 2/2012 |
| GB | 2409951 | 7/2005 |
| WO | WO-93/06237 | 4/1993 |
| WO | WO-96/25089 | 8/1996 |
| WO | WO-96/35370 | 11/1996 |
| WO | WO-97/33513 | 9/1997 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/047445 | 6/2004 |
| WO | WO-2004/061420 | 7/2004 |
| WO | WO-2005/010756 | 2/2005 |
| WO | WO-2005/040404 | 5/2005 |
| WO | WO-2005/041766 | 5/2005 |
| WO | WO-2005/045744 | 5/2005 |
| WO | WO-2005/089103 | 9/2005 |
| WO | WO-2005/119238 | 12/2005 |
| WO | WO-2006/024671 | 3/2006 |
| WO | WO-2006/032653 | 3/2006 |
| WO | WO-2006/051466 | 5/2006 |
| WO | WO-2006/064397 | 6/2006 |
| WO | WO-2006/079114 | 7/2006 |
| WO | WO-2006/085087 | 8/2006 |
| WO | WO-2006/118947 | 11/2006 |
| WO | WO-2006/124099 | 11/2006 |
| WO | WO-2007/007459 | 1/2007 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/097754 | 8/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/077329 | 7/2010 |
| WO | WO-2011/022418 | 2/2011 |

OTHER PUBLICATIONS

Arnold, M. A., et al., "Selectivity on Assessment of Noninvasive Glucose Measurements Based on Analysis of Multivariate Calibration Vectors", *Journal of Diabetes Science and Technology*, vol. 1, No. 4, 2007, pp. 454-462.

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II*, Proceedings of SPIE, vol. 4624, 2002, pp. 1-10.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based 'Wired' Glucose Oxidase", *Analytical Chemistry*, vol. 67, No. 7, on 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Garg, S., et al., "Improvement in Glycemic Excursions with a Transcutaneous, Real-Time Continuous Glucose Sensor", *Diabetes Care*, vol. 29, No. 1, 2006, pp. 44-50.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Li, Y., et al., "In Vivo Release From a Drug Delivery MEMS Device", *Journal of Controlled Release*, vol. 100, 2004, 99. 211-219.

Lo, B., et al., "Key Technical Challenges and Current Implementations of Body Sensor Networks", *Body Sensor Networks*, 2005, pp. 1-5.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

(56) References Cited

OTHER PUBLICATIONS

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences Off-Finger Glucose Testing", *Diabetes on Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 03-mm Amperometric Microsensors", *The American Physiological Society*, 1995, E155-E161.

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

European Patent Application No. 08745803.0, Extended European Search Report mailed Sep. 27, 2012.

European Patent Application No. 08745805.5, Extended European Search Report mailed May 23, 2012.

European Patent Application No. 08745807.1, Extended European Search Report mailed Oct. 8, 2012.

European Patent Application No. 08745809.7, Extended European Search Report mailed Jul. 2, 2012.

European Patent Application No. 08754499.5, Extended European Search Report mailed Sep. 20, 2012.

European Patent Application No. 08871628.7, Extended European Search Report mailed Oct. 15, 2012.

PCT Application No. PCT/US2008/006247, International Preliminary Report on Patentability and Written Opinion of the International Searching Authority mailed Nov. 26, 2009.

PCT Application No. PCT/US2008/006247, International Search Report and Written Opinion of the International Searching Authority mailed Sep. 5, 2008.

PCT Application No. PCT/US2008/060277, International Preliminary Report on Patentability and Written Opinion of the International Searching Authority mailed Oct. 29, 2009.

PCT Application No. PCT/US2008/060277, International Search Report and Written Opinion of the International Searching Authority mailed Sep. 22, 2008.

PCT Application No. PCT/US2008/060279, International Preliminary Report on Patentability and Written Opinion of the International Searching Authority mailed Oct. 29, 2009.

PCT Application No. PCT/US2008/060279, International Search Report and Written Opinion of the International Searching Authority mailed Jul. 14, 2008.

PCT Application No. PCT/US2008/060281, International Preliminary Report on Patentability and Written Opinion of the International Searching Authority mailed Oct. 29, 2009.

PCT Application No. PCT/US2008/060281, International Search Report and Written Opinion of the International Searching Authority mailed Sep. 23, 2008.

PCT Application No. PCT/US2008/060282, International Preliminary Report on Patentability and Written Opinion of the International Searching Authority mailed Oct. 29, 2009.

(56) References Cited

OTHER PUBLICATIONS

PCT Application No. PCT/US2008/060282, International Search Report and Written Opinion of the International Searching Authority mailed Jun. 18, 2009.
PCT Application No. PCT/US2008/060284, International Preliminary Report on Patentability and Written Opinion of the International Searching Authority mailed Oct. 29, 2009.
PCT Application No. PCT/US2008/060284, International Search Report and Written Opinion of the International Searching Authority mailed Sep. 23, 2008.
PCT Application No. PCT/US2008/070923, International Preliminary Report on Patentability and Written Opinion of the International Searching Authority, mailed Feb. 11, 2010.
PCT Application No. PCT/US2008/070923, International Search Report and Written Opinion of the International Searching Authority mailed Oct. 1, 2008.
U.S. Appl. No. 11/831,866, Notice of Allowance mailed May 26, 2010.
U.S. Appl. No. 11/831,866, Office Action mailed Jun. 25, 2009.
U.S. Appl. No. 11/831,866, Supplemental Office Action mailed Dec. 9, 2009.
U.S. Appl. No. 11/831,881, Advisory Action mailed Aug. 23, 2013.
U.S. Appl. No. 11/831,881, Notice of Allowance mailed Jun. 20, 2014.
U.S. Appl. No. 11/831,881, Office Action mailed Jun. 21, 2011.
U.S. Appl. No. 11/831,881, Office Action mailed Mar. 13, 2014.
U.S. Appl. No. 11/831,881, Office Action mailed May 23, 2013.
U.S. Appl. No. 11/831,881, Office Action mailed Nov. 17, 2011.
U.S. Appl. No. 11/831,881, Office Action mailed Oct. 1, 2012.
U.S. Appl. No. 11/831,895, Advisory Action mailed Aug. 5, 2013.
U.S. Appl. No. 11/831,895, Advisory Action mailed Jan. 18, 2012.
U.S. Appl. No. 11/831,895, Advisory Action mailed Jan. 25, 2012.
U.S. Appl. No. 11/831,895, Office Action mailed Jul. 17, 2014.
U.S. Appl. No. 11/831,895, Office Action mailed Jul. 20, 2012.
U.S. Appl. No. 11/831,895, Office Action mailed May 16, 2013.
U.S. Appl. No. 11/831,895, Office Action mailed May 25, 2011.
U.S. Appl. No. 11/831,895, Office Action mailed Oct. 1, 2013.
U.S. Appl. No. 11/831,895, Office Action mailed Oct. 14, 2011.
U.S. Appl. No. 12/102,839, Advisory Action mailed May 1, 2013.
U.S. Appl. No. 12/102,839, Office Action mailed Aug. 1, 2013.
U.S. Appl. No. 12/102,839, Office Action mailed Aug. 5, 2010.
U.S. Appl. No. 12/102,839, Office Action mailed Dec. 14, 2009.
U.S. Appl. No. 12/102,839, Office Action mailed Dec. 14, 2012.
U.S. Appl. No. 12/102,839, Office Action mailed Dec. 5, 2013.
U.S. Appl. No. 12/102,839, Office Action mailed Jan. 25, 2011.
U.S. Appl. No. 12/102,839, Office Action mailed May 25, 2012.
U.S. Appl. No. 12/102,839, Office Action mailed Oct. 27, 2011.
U.S. Appl. No. 12/102,844, Notice of Allowance mailed Jan. 10, 2012.
U.S. Appl. No. 12/102,844, Office Action mailed Aug. 17, 2011.
U.S. Appl. No. 12/102,847, Advisory Action mailed Aug. 27, 2014.
U.S. Appl. No. 12/102,847, Office Action mailed Apr. 24, 2014.
U.S. Appl. No. 12/102,847, Office Action mailed Aug. 18, 2011.
U.S. Appl. No. 12/102,847, Office Action mailed Jan. 10, 2012.
U.S. Appl. No. 12/102,847, Office Action mailed Jun. 16, 2014.
U.S. Appl. No. 12/102,855, Office Action mailed Aug. 24, 2011.
U.S. Appl. No. 12/102,855, Office Action mailed Jan. 10, 2012.
U.S. Appl. No. 12/102,855, Office Action mailed Jun. 11, 2014.
U.S. Appl. No. 12/102,856, Office Action mailed Aug. 17, 2011.
U.S. Appl. No. 12/102,856, Office Action mailed Jan. 10, 2012.
U.S. Appl. No. 12/102,856, Office Action mailed May 7, 2014.
U.S. Appl. No. 12/152,623, Notice of Allowance Mailed Nov. 3, 2011.
U.S. Appl. No. 12/152,623, Office Action mailed May 26, 2011.
U.S. Appl. No. 12/152,636, Advisory Action mailed Jan. 19, 2012.
U.S. Appl. No. 12/152,636, Advisory Action mailed Jan. 6, 2012.
U.S. Appl. No. 12/152,636, Notice of Allowance mailed Jun. 19, 2012.
U.S. Appl. No. 12/152,636, Office Action mailed Dec. 27, 2010.
U.S. Appl. No. 12/152,636, Office Action mailed Sep. 20, 2011.
U.S. Appl. No. 12/152,648, Notice of Allowance mailed Aug. 2, 2013.
U.S. Appl. No. 12/152,648, Office Action mailed Aug. 12, 2011.
U.S. Appl. No. 12/152,648, Office Action mailed Aug. 29, 2012.
U.S. Appl. No. 12/152,648, Office Action mailed Jan. 27, 2012.
U.S. Appl. No. 12/152,648, Office Action mailed Mar. 13, 2013.
U.S. Appl. No. 12/152,649, Notice of Allowance mailed Jul. 1, 2013.
U.S. Appl. No. 12/152,649, Office Action mailed Aug. 5, 2011.
U.S. Appl. No. 12/152,649, Office Action mailed Jan. 27, 2012.
U.S. Appl. No. 12/152,649, Office Action mailed Nov. 5, 2012.
U.S. Appl. No. 12/152,650, Notice of Allowance mailed Jan. 22, 2013.
U.S. Appl. No. 12/152,650, Office Action mailed Aug. 11, 2011.
U.S. Appl. No. 12/152,650, Office Action mailed Jan. 26, 2012.
U.S. Appl. No. 12/152,650, Office Action mailed Jul. 25, 2012.
U.S. Appl. No. 12/152,652, Advisory Action mailed Jan. 13, 2012.
U.S. Appl. No. 12/152,652, Notice of Allowance mailed May 3, 2012.
U.S. Appl. No. 12/152,652, Office Action mailed Jun. 23, 2011.
U.S. Appl. No. 12/152,652, Office Action mailed Nov. 1, 2011.
U.S. Appl. No. 12/152,657, Office Action mailed Aug. 11, 2011.
U.S. Appl. No. 12/152,657, Office Action mailed Jan. 26, 2012.
U.S. Appl. No. 12/152,662, Office Action mailed Aug. 19, 2011.
U.S. Appl. No. 12/152,662, Office Action mailed Jan. 11, 2012.
U.S. Appl. No. 12/152,662, Office Action mailed Jun. 12, 2014.
U.S. Appl. No. 12/152,670, Notice of Allowance mailed Jun. 20, 2011.
U.S. Appl. No. 12/152,670, Office Action mailed Jan. 7, 2011.
U.S. Appl. No. 12/152,673, Advisory Action mailed Apr. 9, 2013.
U.S. Appl. No. 12/152,673, Office Action mailed Aug. 26, 2011.
U.S. Appl. No. 12/152,673, Office Action mailed Jan. 30, 2013.
U.S. Appl. No. 12/152,673, Office Action mailed Jan. 5, 2012.
U.S. Appl. No. 12/152,673, Office Action mailed Jul. 11, 2012.
U.S. Appl. No. 13/356,598, Notice of Allowance mailed Jul. 11, 2013.
U.S. Appl. No. 13/356,598, Office Action mailed Aug. 30, 2012.
U.S. Appl. No. 13/356,598, Office Action mailed May 2, 2013.
U.S. Appl. No. 13/567,038, Notice of Allowance Nov. 22, 2013.
U.S. Appl. No. 13/567,038, Office Action mailed Jun. 6, 2013.
U.S. Appl. No. 13/567,038, Office Action mailed Oct. 10, 2013.
U.S. Appl. No. 13/599,847, Notice of Allowance mailed Aug. 21, 2013.
U.S. Appl. No. 13/599,847, Office Action mailed Jan. 29, 2013.
U.S. Appl. No. 14/106,000, Office Action mailed Aug. 26, 2014.
U.S. Appl. No. 14/106,000, Office Action mailed Jun. 17, 2014.
Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.
Canadian Patent Application No. 2,683,930, Examiner's Report mailed Jul. 22, 2014.
European Patent Application No. 08796500.0, Examination Report mailed Dec. 4, 2014.
European Patent Application No. 08796500.0, Extended European Search Report mailed Jan. 14, 2014.
U.S. Appl. No. 11/831,895, Office Action mailed Feb. 13, 2015.
U.S. Appl. No. 12/102,847, Office Action mailed Feb. 12, 2015.
U.S. Appl. No. 12/102,855, Office Action mailed Oct. 24, 2014.
U.S. Appl. No. 12/102,856, Notice of Allowance mailed Feb. 25, 2015.
U.S. Appl. No. 12/102,856, Office Action mailed Nov. 25, 2014.
U.S. Appl. No. 12/152,657, Office Action mailed Sep. 18, 2014.
U.S. Appl. No. 12/152,662, Advisory Action mailed Sep. 3, 2014.
U.S. Appl. No. 12/152,662, Office Action mailed Jan. 23, 2015.
U.S. Appl. No. 14/106,000, Office Action mailed Nov. 26, 2014.

* cited by examiner

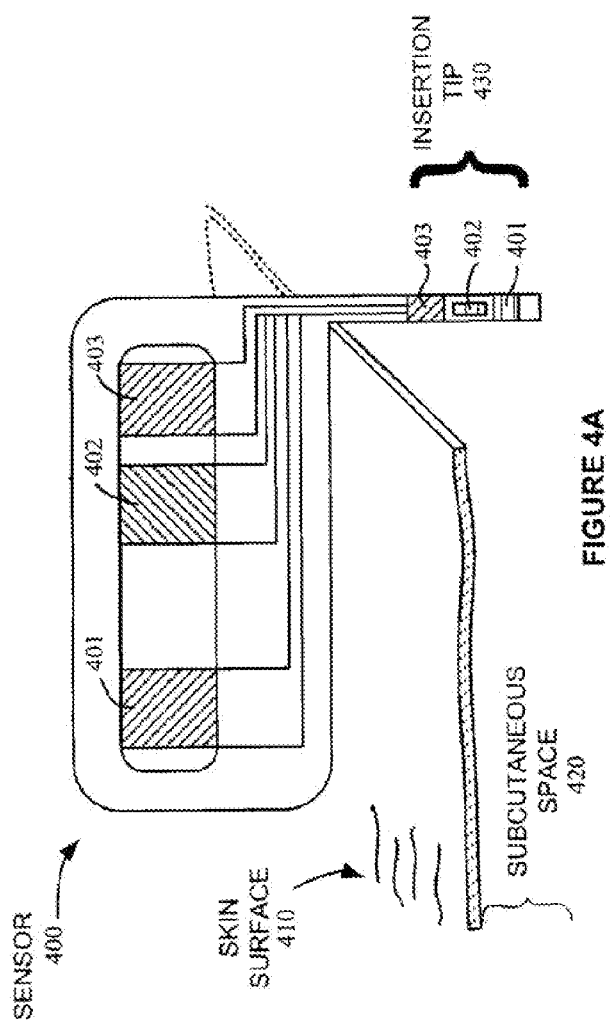
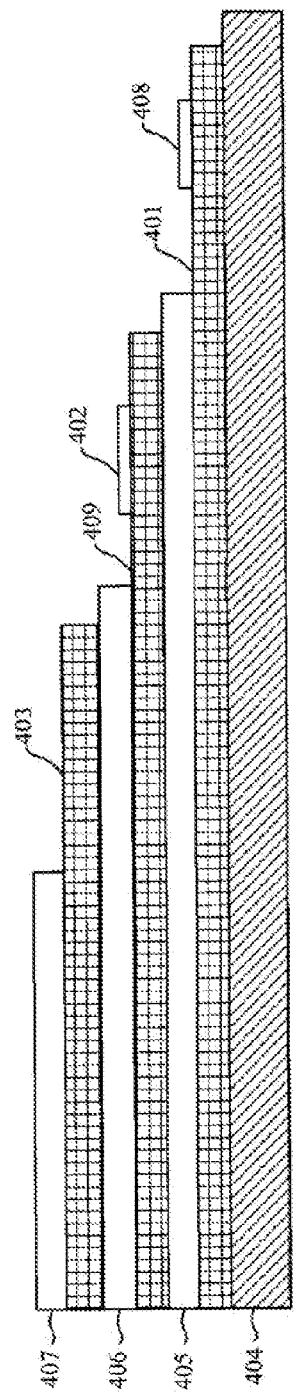
FIGURE 4A
FIGURE 4B

METHOD AND APPARATUS FOR PROVIDING ANALYTE SENSOR CALIBRATION

RELATED APPLICATION

The present application is a continuation of U.S. patent application Ser. No. 11/831,881 filed Jul. 31, 2007, now U.S. Pat. No. 8,834,366, entitled "Method and Apparatus for Providing Analyte Sensor Calibration," the disclosure of which is incorporated herein by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels. To provide flexibility in analyte sensor manufacturing and/or design, among others, tolerance of a larger range of the analyte sensor sensitivities for processing by the transmitter unit is desirable.

In view of the foregoing, it would be desirable to have a method and system for providing data processing and control for use in medical telemetry systems such as, for example, analyte monitoring systems.

SUMMARY

In one embodiment, method and apparatus for, prior to calibrating an in vivo analyte sensor, retrieving one or more parameters to calibrate the analyte sensor data, analyzing the retrieved one or more parameters to determine whether the analyte sensor data calibration will fail, and generating a notification based on the analysis of the retrieved one or more parameters, is disclosed.

These and other objects, features and advantages of the present invention will become more fully apparent from the following detailed description of the embodiments, the appended claims and the accompanying drawings.

BRIEF DESCRIPTION OF THE DRAWINGS

FIGS. 4A-4B illustrate a perspective view and a cross sectional view, respectively of an analyte sensor in accordance with one embodiment of the present invention;

DETAILED DESCRIPTION

As described in further detail below, in accordance with the various embodiments of the present invention, there is provided a method and apparatus for providing data processing and control for use in a medical telemetry system. In particular, within the scope of the present invention, there are provided a method and system for providing data communication and control for use in a medical telemetry system such as, for example, a continuous glucose monitoring system.

Figure 1:
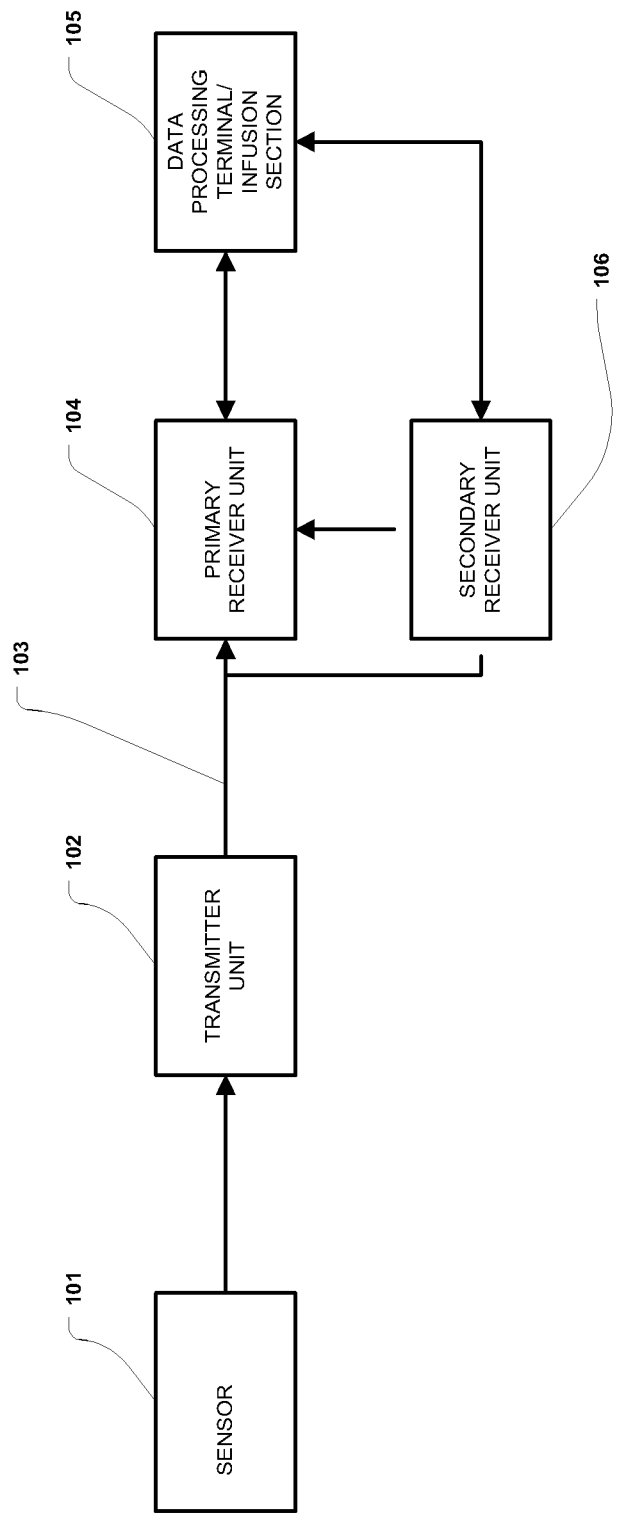
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to the sensor 101 so that both devices are positioned on the user's body, with at least a portion of the analyte sensor 101 positioned transcutaneously under the skin layer of the user. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via a communication link, where the communication link, as described above, may be configured for bi-directional communication.

In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a BLUETOOTH® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
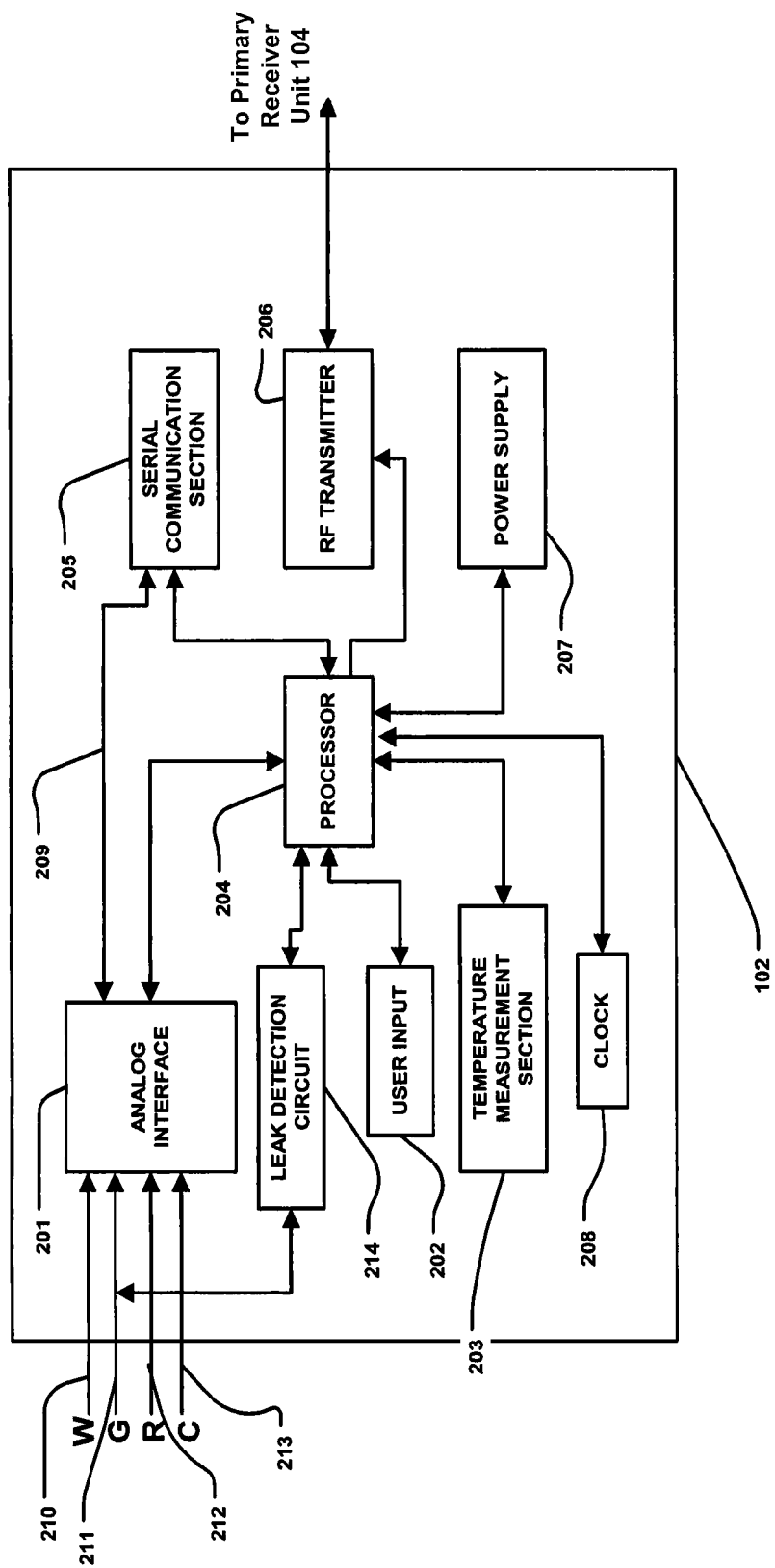
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature measurement section 203, each of which is operatively coupled to a transmitter processor 204 such as a central processing unit (CPU).

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

As can be seen from FIG. 2, the sensor 101 (FIG. 1) is provided four contacts, three of which are electrodes—work electrode (W) 210, guard contact (G) 211, reference electrode (R) 212, and counter electrode (C) 213, each operatively coupled to the analog interface 201 of the transmitter unit 102. In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched, or alternatively provided on a substrate material using laser or photolithography.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature measurement section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Figure 3:
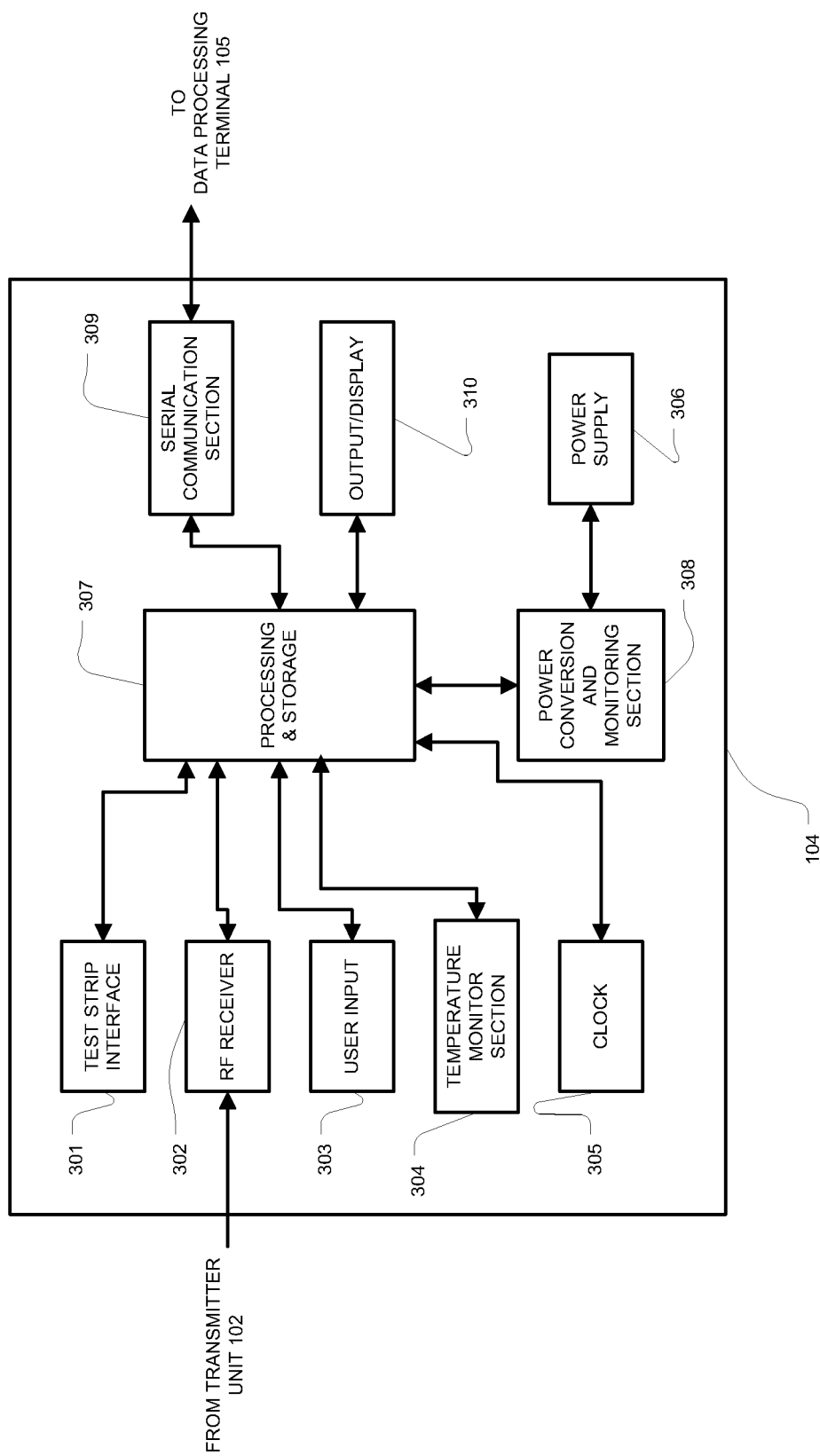
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature monitor section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature monitor section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

In a further embodiment, the one or more of the transmitter unit 102, the primary receiver unit 104, secondary receiver unit 106, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 106, or the data processing terminal/infusion section 105.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003, now U.S. Pat. No. 7,811,231, entitled "Continuous Glucose Monitoring System and Methods of Use", each assigned to the Assignee of the present application.

FIGS. 4A-4B illustrate a perspective view and a cross sectional view, respectively of an analyte sensor in accordance with one embodiment of the present invention. Referring to FIG. 4A, a perspective view of a sensor 400, the major portion of which is above the surface of the skin 410, with an insertion tip 430 penetrating through the skin and into the subcutaneous space 420 in contact with the user's biofluid such as interstitial fluid. Contact portions of a working electrode 401, a reference electrode 402, and a counter electrode 403 can be seen on the portion of the sensor 400 situated above the skin surface 410. Working electrode 401, a reference electrode 402, and a counter electrode 403 can be seen at the end of the insertion tip 430.

Referring now to FIG. 4B, a cross sectional view of the sensor 400 in one embodiment is shown. In particular, it can be seen that the various electrodes of the sensor 400 as well as the substrate and the dielectric layers are provided in a stacked or layered configuration or construction. For example, as shown in FIG. 4B, in one aspect, the sensor 400 (such as the sensor 101 FIG. 1), includes a substrate layer 404, and a first conducting layer 401 such as a carbon trace disposed on at least a portion of the substrate layer 404, and which may comprise the working electrode. Also shown disposed on at least a portion of the first conducting layer 401 is a sensing layer 408.

Referring back to FIG. 4B, a first insulation layer such as a first dielectric layer 405 is disposed or stacked on at least a portion of the first conducting layer 401, and further, a second conducting layer 409 such as another carbon trace may be disposed or stacked on top of at least a portion of the first insulation layer (or dielectric layer) 405. As shown in FIG. 4B, the second conducting layer 409 may comprise the reference electrode 402, and in one aspect, may include a layer of silver/silver chloride (Ag/AgCl).

Referring still again to FIG. 4B, a second insulation layer 406 such as a dielectric layer in one embodiment may be disposed or stacked on at least a portion of the second conducting layer 409. Further, a third conducting layer 403 which may include carbon trace and that may comprise the counter electrode 403 may in one embodiment be disposed on at least a portion of the second insulation layer 406. Finally, a third insulation layer 407 is disposed or stacked on at least a portion of the third conducting layer 403. In this manner, the sensor 400 may be configured in a stacked or layered construction or configuration such that at least a portion of each of the conducting layers is separated by a respective insulation layer (for example, a dielectric layer).

Additionally, within the scope of the present invention, some or all of the electrodes 401, 402, 403 may be provided on the same side of the substrate 404 in a stacked construction as described above, or alternatively, may be provided in a co-planar manner such that each electrode is disposed on the same plane on the substrate 404, however, with a dielectric material or insulation material disposed between the conducting layers/electrodes. Furthermore, in still another aspect of the present invention, the one or more conducting layers such as the electrodes 401, 402, 403 may be disposed on opposing sides of the substrate 404.

Referring back to the Figures, in one embodiment, the transmitter unit 102 (FIG. 1) is configured to detect the current signal from the sensor 101 (FIG. 1) and the skin temperature near the sensor 101, which are preprocessed by, for example, the transmitter processor 204 (FIG. 2) and transmitted to the receiver unit (for example, the primary receiver unit 104 (FIG. 1)) periodically at a predetermined time interval, such as for example, but not limited to, once per minute, once every two minutes, once every five minutes, or once every ten minutes. Additionally, the transmitter unit 102 may be configured to perform sensor insertion and/or removal detection and data quality analysis, information pertaining to which are also transmitted to the receiver unit 104 periodically at the predetermined time interval. In turn, the receiver unit 104 may be configured to perform, for example, skin temperature compensation as well as calibration of the sensor data received from the transmitter 102.

For example, in one aspect, the transmitter unit 102 may be configured to oversample the sensor signal at a nominal rate of four samples per second, which allows the analyte anti-aliasing filter in the transmitter unit 102 to attenuate noise (for example, due to effects resulting from motion or movement of the sensor after placement) at frequencies above 2 Hz. More specifically, in one embodiment, the transmitter processor 204 may be configured to include a digital filter to reduce aliasing noise when decimating the four Hz sampled sensor data to once per minute samples for transmission to the receiver unit 104. As discussed in further detail below, in one aspect, a two stage Kaiser Finite Impulse Response (FIR) filter may be used to perform the digital filtering for anti-aliasing. While Kaiser FIR filter may be used for digital filtering of the sensor signals, within the scope of the present disclosure, other suitable filters may be used to filter the sensor signals.

In one aspect, the temperature measurement section 203 of the transmitter unit 102 may be configured to measure once per minute the on skin temperature near the analyte sensor at the end of the minute sampling cycle of the sensor signal. Within the scope of the present disclosure, different sample rates may be used which may include, for example, but are not limited to, measuring the on skin temperature for each 30 second periods, each two minute periods, and the like. Additionally, as discussed above, the transmitter unit 102 may be configured to detect sensor insertion, sensor signal settling after sensor insertion, and sensor removal, in addition to detecting for sensor—transmitter system failure modes and sensor signal data integrity. Again, this information is transmitted periodically by the transmitter unit 102 to the receiver unit 104 along with the sampled sensor signals at the predetermined time intervals.

Referring again to the Figures, as the analyte sensor measurements are affected by the temperature of the tissue around the transcutaneously positioned sensor 101, in one aspect, compensation of the temperature variations and affects on the sensor signals are provided for determining the corresponding glucose value. Moreover, the ambient temperature around the sensor 101 may affect the accuracy of the on skin temperature measurement and ultimately the glucose value determined from the sensor signals. Accordingly, in one aspect, a second temperature sensor is provided in the transmitter unit 102 away from the on skin temperature sensor (for example, physically away from the temperature measurement section 203 of the transmitter unit 102), so as to provide compensation or correction of the on skin temperature measurements due to the ambient temperature effects. In this manner, the accuracy of the estimated glucose value corresponding to the sensor signals may be attained.

In one aspect, the processor 204 of the transmitter unit 102 may be configured to include the second temperature sensor, and which is located closer to the ambient thermal source within the transmitter unit 102. In other embodiments, the second temperature sensor may be located at a different location within the transmitter unit 102 housing where the ambient temperature within the housing of the transmitter unit 102 may be accurately determined.

Figure 5:
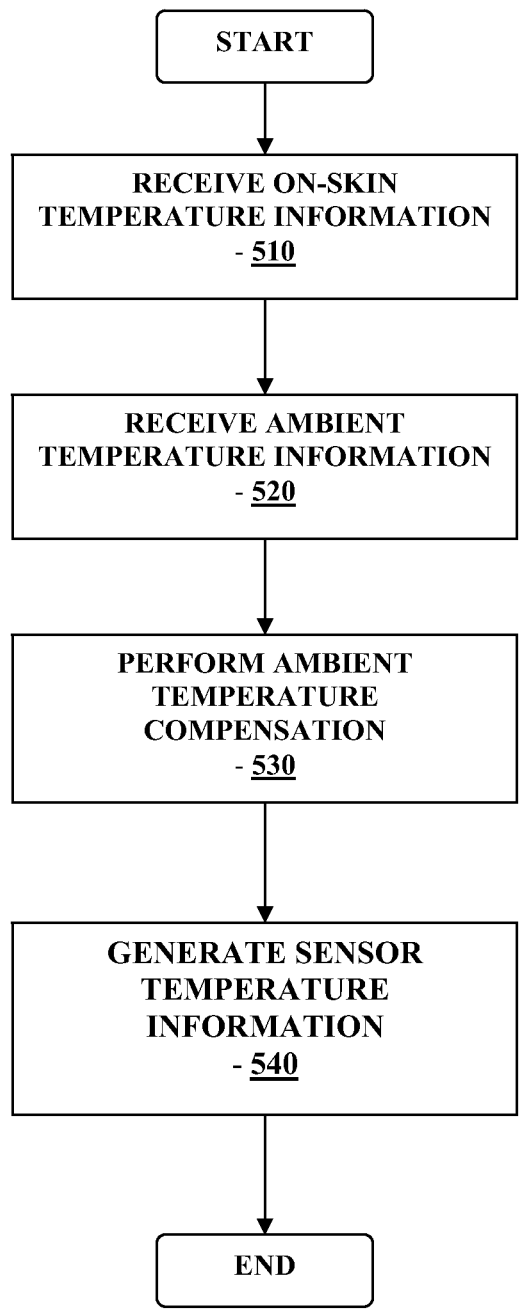
FIG. 5 is a flowchart illustrating ambient temperature compensation routine for determining on-skin temperature information in accordance with one embodiment of the present invention.

Referring now to FIG. 5, in one aspect, an ambient temperature compensation routine for determining the on-skin temperature level for use in the glucose estimation determination based on the signals received from the sensor 101 is disclosed. Referring to FIG. 5, for each sampled signal from the sensor 101, a corresponding measured temperature information is received (510), for example, by the processor 204 from the temperature measurement section 203 (which may include, for example, a thermistor provided in the transmitter unit 102). In addition, a second temperature measurement is obtained (520), for example, including a determination of the ambient temperature level using a second temperature sensor provided within the housing of the transmitter unit 102. In one aspect, the measured on-skin temperature information (510) and the ambient temperature information (520) may be received substantially simultaneously, or in a further aspect, the ambient temperature information (520) may be received prior to or after the measured on-skin temperature information (510).

In one aspect, based on a predetermined ratio of thermal resistances between the temperature measurement section 203 and the second temperature sensor (located, for example, within the processor 204 of the transmitter unit 102), and between the temperature measurement section 203 and the skin layer on which the transmitter unit 102 is placed and coupled to the sensor 101, ambient temperature compensation may be performed (530), to determine the corresponding ambient temperature compensated on skin temperature level (540). In one embodiment, the predetermined ratio of the thermal resistances may be approximately 0.2. However, within the scope of the present invention, this thermal resistance ratio may vary according to the design of the system, for example, based on the size of the transmitter unit 102 housing, the location of the second temperature sensor within the housing of the transmitter unit 102, as well as based on, for example, one or more complex compensation modeling algorithms such as a linear model with an offset, a polynomial model and the like.

With the ambient temperature compensated on-skin temperature information, the corresponding glucose value from the sampled analyte sensor signal may be determined.

Referring again to FIG. 2, the processor 204 of the transmitter unit 102 may include a digital anti-aliasing filter. Using analog anti-aliasing filters for a one minute measurement data sample rate would require a large capacitor in the transmitter unit 102 design, and which in turn impacts the size of the transmitter unit 102. As such, in one aspect, the sensor signals may be oversampled (for example, at a rate of 4 times per second), and then the data is digitally decimated to derive a one-minute sample rate.

As discussed above, in one aspect, the digital anti-aliasing filter may be used to remove, for example, signal artifacts or otherwise undesirable aliasing effects on the sampled digital signals received from the analog interface 201 of the transmitter unit 102. For example, in one aspect, the digital anti-aliasing filter may be used to accommodate decimation of the sensor data from approximately four Hz samples to one-minute samples. In one aspect, a two stage FIR filter may be used for the digital anti-aliasing filter, and which includes improved response time, pass band and stop band properties.

Figure 6:
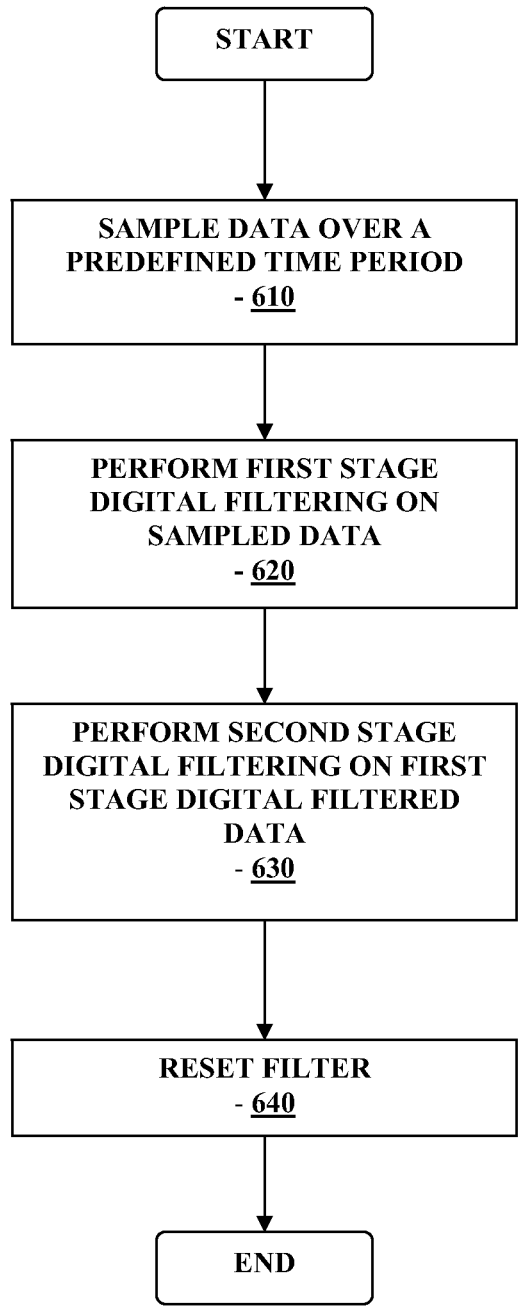
FIG. 6 is a flowchart illustrating digital anti-aliasing filtering routing in accordance with one embodiment of the present invention.

Referring to FIG. 6, a routine for digital anti-aliasing filtering is shown in accordance with one embodiment. As shown, in one embodiment, at each predetermined time period such as every minute, the analog signal from the analog interface 201 corresponding to the monitored analyte level received from the sensor 101 (FIG. 1) is sampled (610). For example, at every minute, in one embodiment, the signal from the analog interface 201 is over-sampled at approximately 4 Hz. Thereafter, the first stage digital filtering on the over-sampled data is performed (620), where, for example, a 1/6 down-sampling from 246 samples to 41 samples is performed, and the resulting 41 samples is further down-sampled at the second stage digital filtering (630) such that, for example, a 1/41 down-sampling is performed from 41 samples (from the first stage digital filtering), to a single sample. Thereafter, the filter is reset (640), and the routine returns to the beginning for the next minute signal received from the analog interface 201.

While the use of FIR filter, and in particular the use of Kaiser FIR filter, is within the scope of the present invention, other suitable filters, such as FIR filters with different weighting schemes or Infinite Impulse Response (IIR) filters, may be used.

Referring yet again to the Figures, the transmitter unit 102 may be configured in one embodiment to periodically perform data quality checks including error condition verifications and potential error condition detections, and also to transmit the relevant information related to one or more data quality, error condition or potential error condition detection to the receiver unit 104 with the transmission of the monitored sensor data. For example, in one aspect, a state machine may be used in conjunction with the transmitter unit 102 and which may be configured to be updated four times per second, the results of which are transmitted to the receiver unit 104 every minute.

In particular, using the state machine, the transmitter unit 102 may be configured to detect one or more states that may indicate when a sensor is inserted, when a sensor is removed from the user, and further, may additionally be configured to perform related data quality checks so as to determine when a new sensor has been inserted or transcutaneously positioned under the skin layer of the user and has settled in the inserted state such that the data transmitted from the transmitter unit 102 does not compromise the integrity of signal processing performed by the receiver unit 104 due to, for example, signal transients resulting from the sensor insertion.

That is, when the transmitter unit 102 detects low or no signal from the sensor 101, which is followed by detected signals from the sensor 101 that is above a given signal, the processor 204 may be configured to identify such transition in the monitored signal levels and associate with a potential sensor insertion state. Alternatively, the transmitter unit 102 may be configured to detect the signal level above the other predetermined threshold level, which is followed by the detection of the signal level from the sensor 101 that falls below the predetermined threshold level. In such a case, the processor 204 may be configured to associate or identify such transition or condition in the monitored signal levels as a potential sensor removal state.

Accordingly, when either of potential sensor insertion state or potential sensor removal state is detected by the transmitter unit 102, this information is transmitted to the receiver unit 104, and in turn, the receiver unit may be configured to prompt the user for confirmation of either of the detected potential sensor related state. In another aspect, the sensor insertion state or potential sensor removal state may be detected or determined by the receiver unit based on one or more signals received from the transmitter unit 102. For example, similar to an alarm condition or a notification to the user, the receiver unit 104 may be configured to display a request or a prompt on the display or an output unit of the receiver unit 104 a text and/or other suitable notification message to inform the user to confirm the state of the sensor 101.

For example, the receiver unit 104 may be configured to display the following message: "New Sensor Inserted?" or a similar notification in the case where the receiver unit 104 receives one or more signals from the transmitter unit 102 associated with the detection of the signal level below the predetermined threshold level for the predefined period of time, followed by the detection of the signal level from the sensor 101 above another predetermined threshold level for another predefined period of time. Additionally, the receiver unit 104 may be configured to display the following message: "Sensor Removed?" or a similar notification in the case where the receiver unit 104 received one or more signals from the transmitter unit 102 associated with the detection of the signal level from the sensor 101 that is above another predetermined threshold level for another predefined period of time, which is followed by the detection of the signal level from the sensor 101 that falls below the predetermined threshold level for the predefined period of time.

Based on the user confirmation received, the receiver unit 104 may be further configured to execute or perform additional related processing and routines in response to the user confirmation or acknowledgement. For example, when the user confirms, using the user interface input/output mechanism of the receiver unit 104, for example, that a new sensor has been inserted, the receiver unit 104 may be configured to initiate new sensor insertion related routines including, such as, for example, a sensor calibration routine including, for example, calibration timer, sensor expiration timer and the like. Alternatively, when the user confirms or it is determined that the sensor 101 is not properly positioned or otherwise removed from the insertion site, the receiver unit 104 may be accordingly configured to perform related functions such as, for example, stop displaying of the glucose values/levels, or deactivating the alarm monitoring conditions.

On the other hand, in response to the potential sensor insertion notification generated by the receiver unit 104, if the user confirms that no new sensor has been inserted, then the receiver unit 104 in one embodiment is configured to assume that the sensor 101 is in acceptable operational state, and continues to receive and process signals from the transmitter unit 102.

In this manner, in cases, for example, when there is momentary movement or temporary dislodging of the sensor 101 from the initially positioned transcutaneous state, or when one or more of the contact points between sensor 101 and the transmitter unit 102 are temporarily disconnected, but otherwise, the sensor 101 is operational and within its useful life, the routine above provides an option to the user to maintain the usage of the sensor 101, and not replacing the sensor 101 prior to the expiration of its useful life. In this manner, in one aspect, false positive indications of sensor 101 failure may be identified and addressed.

Figure 7:
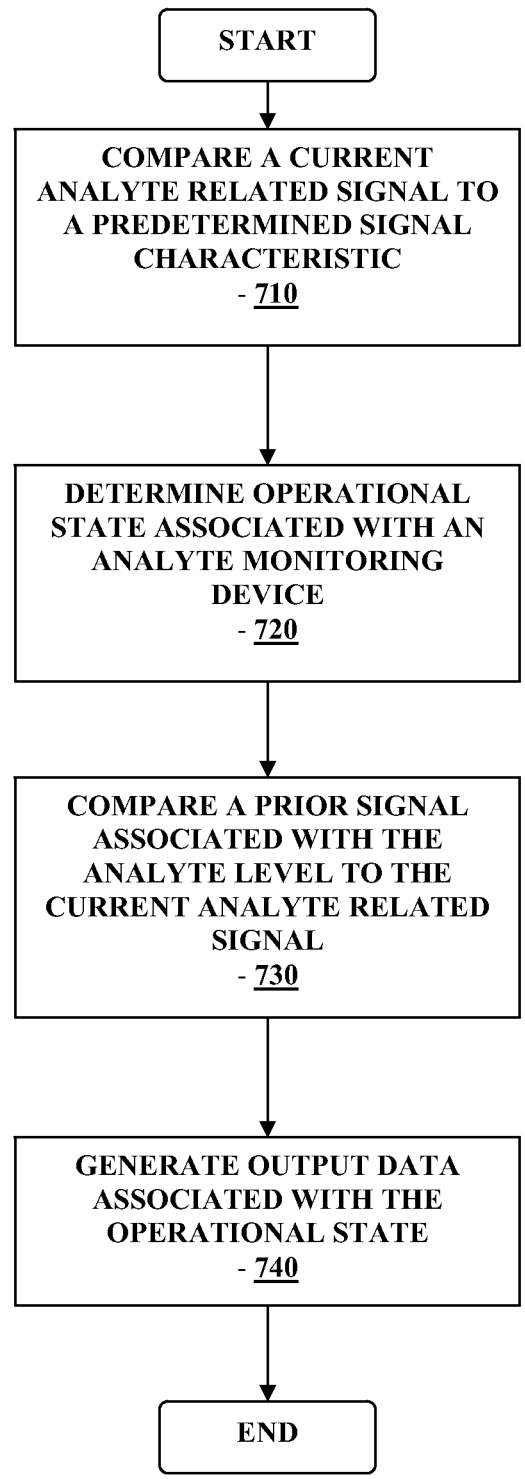
FIG. 7 is a flowchart illustrating actual or potential sensor insertion or removal detection routine in accordance with one embodiment of the present invention.

For example, FIG. 7 is a flowchart illustrating actual or potential sensor insertion or removal detection routine in accordance with one embodiment of the present invention. Referring to the Figure, the current analyte related signal is first compared to a predetermined signal characteristic (710). In one aspect, the predetermined signal characteristic may include one of a signal level transition from below a first predetermined level (for example, but not limited to 18 ADC (analog to digital converter) counts) to above the first predetermined level, a signal level transition from above a second predetermined level (for example, but not limited to 9 ADC counts) to below the second predetermined level, a transition from below a predetermined signal rate of change threshold to above the predetermined signal rate of change threshold, and a transition from above the predetermined signal rate of change threshold to below the predetermined signal rate of change threshold. Moreover, in another aspect, the predetermined signal characteristic may include the determination of the current analyte related signal maintained at the transitioned signal state for a predetermined time period, such as, for example, approximately 10 seconds. That is, referring to FIG. 7, in one embodiment, the current analyte related signal may be compared to the predetermined signal characteristic such that it is determined that the current analyte related signal has transitioned from one state to another as described above, and further, that the current analyte related signal is maintained at the transitioned signal level/characteristic for a given time period.

Referring back to the Figure, after comparing the current analyte related signal to the predetermined signal characteristic (710), a corresponding operational state associated with an analyte monitoring device is determined (720). That is, in one aspect, based on the one or more of the signal level transition discussed above, the corresponding operational state of the analyte monitoring device such as, for example, the operational state of the analyte sensor 101 (FIG. 1) may be determined. Referring again to FIG. 7, after determining the corresponding operational state associated with the analyte monitoring device (720), the current analyte related signal may be compared to a prior signal associated with the analyte level (730) and an output data associated with the operational state is generated (740). That is, in one aspect, an output indication representative of the determined sensor operational state may be provided.

In this manner, in one aspect of the present invention, based on a transition state of the received analyte related signals, it may be possible to determine the state of the analyte sensor and, based on which, the user or the patient may confirm whether the analyte sensor is in the desired or proper position, has been temporarily dislocated, or otherwise, removed from the desired insertion site so as to require a new analyte sensor.

In this manner, in one aspect, when the monitored signal from the sensor 101 crosses a transition level (for example, from no or low signal level to a high signal level, or vice versa), the transmitter unit 102 may be configured to generate an appropriate output data associated with the sensor signal transition, for transmission to the receiver unit 104 (FIG. 1). Additionally, as discussed in further detail below, in another embodiment, the determination of whether the sensor 101 has crossed a transition level may be determined by the receiver/monitor unit 104/106 based, at least in part, on the one or more signals received from the transmitter unit 102.

Figure 8:
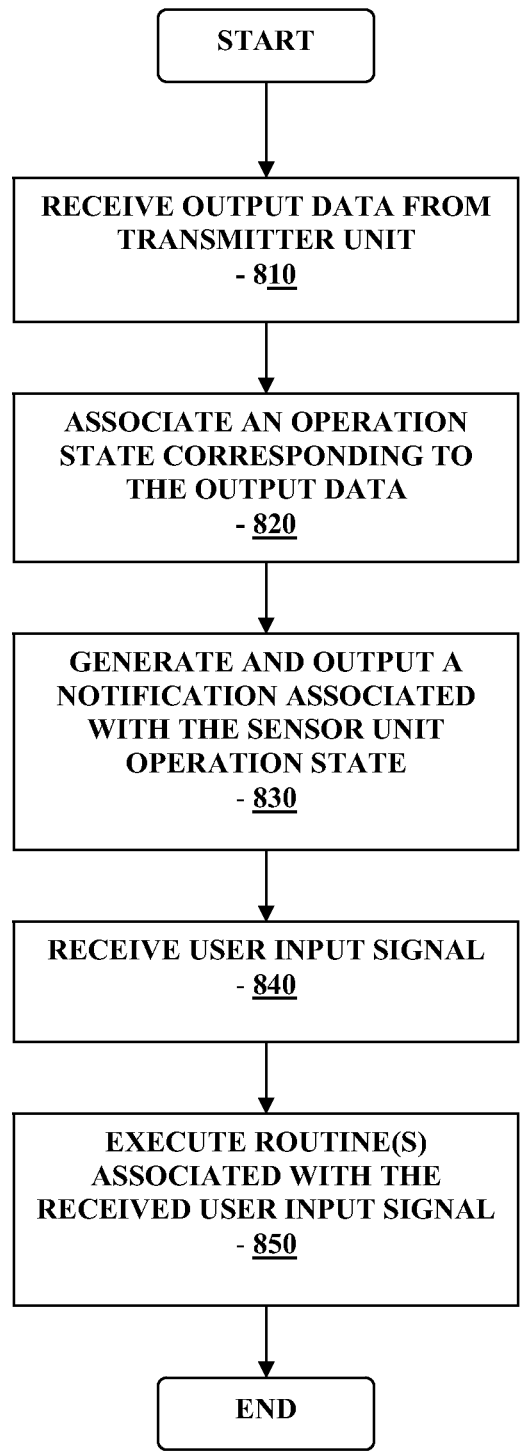
FIG. 8 is a flowchart illustrating receiver unit processing corresponding to the actual or potential sensor insertion or removal detection routine of FIG. 7 in accordance with one embodiment of the present invention.

FIG. 8 is a flowchart illustrating receiver unit processing corresponding to the actual or potential sensor insertion or removal detection routine of FIG. 7 in accordance with one embodiment of the present invention. Referring now to FIG. 8, when the receiver unit 104 receives the generated output data from the transmitter unit 102 (810), a corresponding operational state is associated with the received output data (820), for example, related to the operational state of the sensor 101. Moreover, a notification associated with the sensor operational state is generated and output to the user on the display unit or any other suitable output segment of the receiver unit 104 (830). When a user input signal is received in response to the notification associated with the sensor operational state (840), the receiver unit 104 is configured to execute one or more routines associated with the received user input signal (850).

That is, as discussed above, in one aspect, if the user confirms that the sensor 101 has been removed, the receiver unit 104 may be configured to terminate or deactivate alarm monitoring and glucose displaying functions. On the other hand, if the user confirms that a new sensor 101 has been positioned or inserted into the user, then the receiver unit 104 may be configured to initiate or execute routines associated with the new sensor insertion, such as, for example, calibration procedures, establishing calibration timer, and establishing sensor expiration timer.

In a further embodiment, based on the detected or monitored signal transition, the receiver/monitor unit may be configured to determine the corresponding sensor state without relying upon the user input or confirmation signal associated with whether the sensor is dislocated or removed from the insertion site, or otherwise, operating properly.

Figure 9:
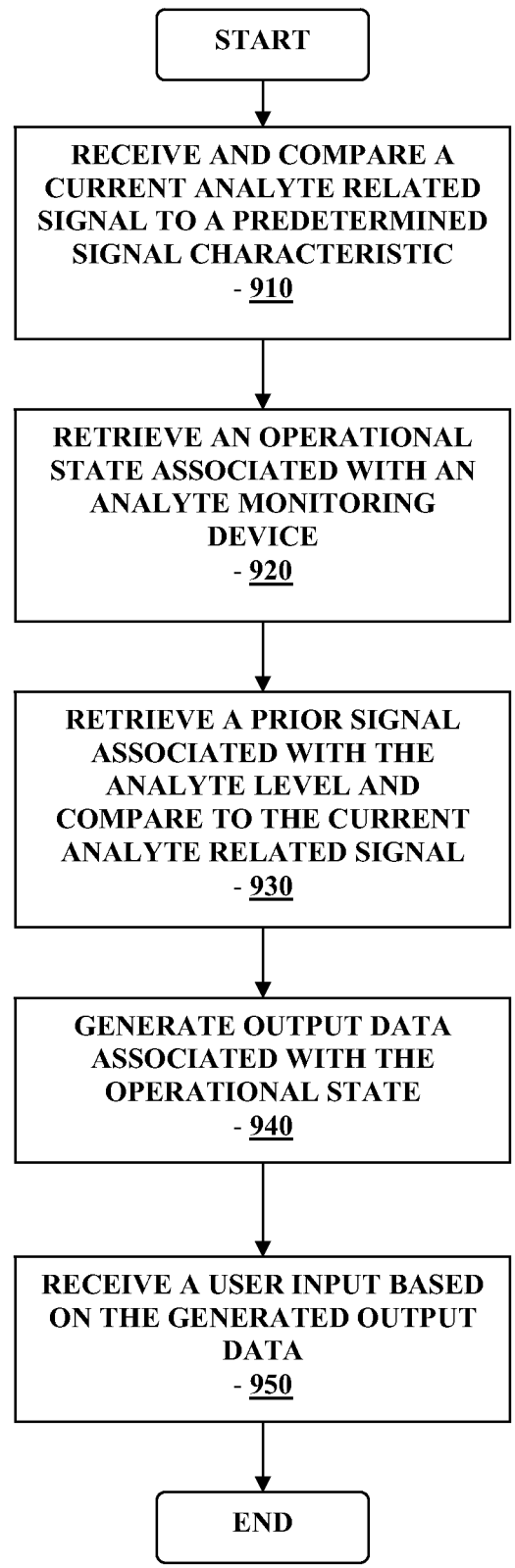
FIG. 9 is a flowchart illustrating data processing corresponding to the actual or potential sensor insertion or removal detection routine in accordance with another embodiment of the present invention.

FIG. 9 is a flowchart illustrating data processing corresponding to the actual or potential sensor insertion or removal detection routine in accordance with another embodiment of the present invention. Referring to FIG. 9, a current analyte related signal is received and compared to a predetermined signal characteristic (910). Thereafter, an operational state associated with an analyte monitoring device such as, for example, the sensor 101 (FIG. 1) is retrieved (920) from a storage unit or otherwise resident in, for example, a memory of the receiver/monitor unit 104/106. An output data is generated which is associated with the operational state (940), and which at least in part is based on the one or more of the received current analyte related signal and the retrieved prior analyte related signal (930).

Referring again to FIG. 9, when the output data is generated (940), a corresponding user input command or signal is received in response to the generated output data (950), and which may include one or more of a confirmation, verification, or rejection of the operational state related to the analyte monitoring device.

Figure 10:
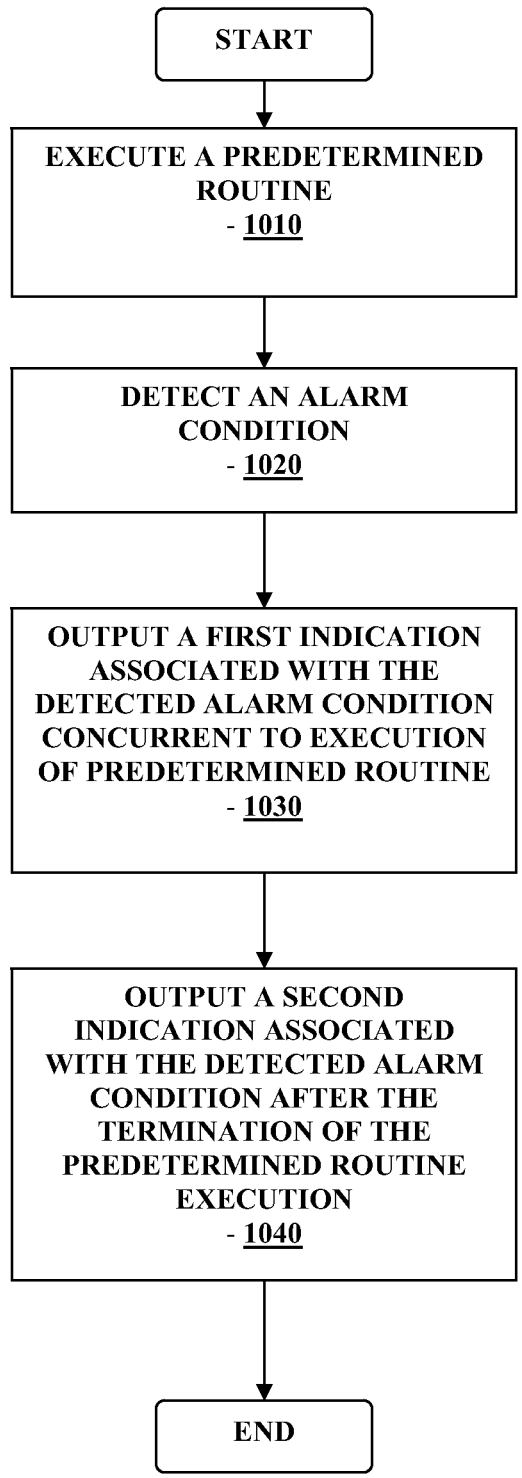
FIG. 10 is a flowchart illustrating a concurrent passive notification routine in the data receiver/monitor unit of the data monitoring and management system of FIG. 1 in accordance with one embodiment of the present invention.

FIG. 10 is a flowchart illustrating a concurrent passive notification routine in the data receiver/monitor unit of the data monitoring and management system of FIG. 1 in accordance with one embodiment of the present invention. Referring to FIG. 10, a predetermined routine is executed for a time period to completion (1010). During the execution of the predetermined routine, an alarm condition is detected (1020), and when the alarm or alert condition is detected, a first indication associated with the detected alarm or alert condition is output concurrent to the execution of the predetermined routine (1030).

That is, in one embodiment, when a predefined routine is being executed, and an alarm or alert condition is detected, a notification is provided to the user or patient associated with the detected alarm or alert condition, but which does not interrupt or otherwise disrupt the execution of the predefined routine. Referring back to FIG. 10, upon termination of the predetermined routine, another output or second indication associated with the detected alarm condition is output or displayed (1040).

More specifically, in one aspect, the user interface notification feature associated with the detected alarm condition is output to the user only upon the completion of an ongoing routine which was in the process of being executed when the alarm condition is detected. As discussed above, when such alarm condition is detected during the execution of a predetermined routine, an alarm notification such as, for example, a backlight indicator, an icon, a modification in any display item feature such as a border around a field that flashes, or a text output on the user interface display or any other suitable output indication may be provided to alert the user or the patient of the detected alarm condition substantially in real time, but which does not disrupt an ongoing routine.

Within the scope of the present disclosure, the ongoing routine or the predetermined routine being executed may include one or more of performing a blood glucose test (for example, for purposes of periodically calibrating the sensor 101), or any other processes that interface with the user interface, for example, on the receiver/monitor unit 104/106 (FIG. 1) including, but not limited to the configuration of device settings, review of historical data such as glucose data, alarms, events, entries in the data log, visual displays of data including graphs, lists, and plots, data communication management including RF communication administration, data transfer to the data processing terminal 105 (FIG. 1), or viewing one or more alarm conditions with a different priority in a preprogrammed or determined alarm or notification hierarchy structure.

In this manner, in one aspect of the present invention, the detection of one or more alarm conditions may be presented or notified to the user or the patient, without interrupting or disrupting an ongoing routine or process in, for example, the receiver/monitor unit 104/106 or the data monitoring and management system 100 (FIG. 1).

Referring again to the Figures, in one aspect, the transmitter unit 102 may be configured to perform one or more periodic or routine data quality check or verification before transmitting the data packet to the receiver/monitor unit 104/106. For example, in one aspect, for each data transmission (e.g., every 60 seconds, or some other predetermined transmission time interval), the transmitter data quality flags in the data packet are reset, and then it is determined whether any data fields in the transmission data packet includes an error flag. If one error flag is detected, then in one aspect, the entire data packet may be considered corrupt, and this determination is transmitted to the receiver/monitor unit 104/106. Alternatively, the determination that the entire data packet is corrupt may be performed by the receiver/monitor unit 104/106. Accordingly, in one aspect, when at least one data quality check fails in the transmitter data packet, the entire packet is deemed to be in error, and the associated monitored analyte level is discarded, and not further processed by the receiver/monitor unit 104/106.

In a further aspect, when an error flag is included in the data packet, the receiver monitor unit 104/106 may be configured to determine the level or degree of signal degradation or corruptness, and further, may utilize the data in one or more further routines.

In another aspect, the data quality check in the transmitter unit 102 data packet may be performed so as to identify each error flag in the data packet, and those identified error flag are transmitted to the receiver/monitor unit 104/106 in addition to the associated monitored analyte level information. In this manner, in one aspect, if the error flag is detected in the transmitter data packet which is not relevant to the accuracy of the data associated with the monitored analyte level, the error indication is flagged and transmitted to the receiver/monitor unit 104/106 in addition to the data indicating the monitored analyte level. In a further aspect, when one or more error flags is identified in the transmitter unit 102 data packet, the transmitter unit 102 data packet may not be transmitted, but rather, the error flags may be transmitted and not the associated data. Alternatively, the transmitted data from the transmitter unit 102 may include the error flags as well as the associated data.

In one aspect, examples of error condition that may be detected or flagged in the transmitter unit 102 data packet include sensor connection fault verification by, for example, determining, among others, whether the monitored analyte level signal is within a predetermined range, whether the counter electrode voltage signal is within a predetermined range, one or more rate of changes of the monitored analyte level deviating from a predetermined threshold level, transmitter unit temperature (ambient and/or on-skin temperature) out of range, and the like. As discussed above, the data quality check in the transmitter unit 102 may be performed serially, such that detection of an error condition or an error flag renders the entire data packet invalid or deemed corrupt. In this case, such data is reported as including error to the receiver/monitor unit 104/106, but not used to process the associated monitored analyte level.

In another aspect, all data quality fields in the data packet of the transmitter unit 102 may be checked for error flags, and if there are error flags detected, the indication of the detected error flags is transmitted with the data packet to the receiver/monitor unit 104/106 for further processing. Alternatively, the transmitter unit 102 may be configured to transmit the data packet with the error flags to the receiver/monitor unit 104/106, and where the above-described error checking/verification routine is performed by the receiver/monitor unit 104/106.

In one embodiment, on the receiver/monitor unit 104/106 side, for each periodic data packet received (for example every 60 seconds or some other predetermined time interval), the receiver/monitor unit 104/106 may be configured to receive the raw glucose data including any data quality check flags from the transmitter unit 102, and to apply temperature compensation and/or calibration to the raw data to determine the corresponding glucose data (accounting for any data quality flags as may have been identified). The unfiltered, temperature compensated and/or calibrated glucose data is stored along with any data quality flags in a FIFO buffer (including, for example, any invalid data identifier). Alternatively, a further data quality check may be performed by the receiver/monitor unit 104/106 on the temperature compensated and calibrated glucose data to determine the rate of change or variance of the measured glucose data. For example, in one embodiment, a high variance check or verification is performed on 15 minutes of glucose data stored in the FIFO buffer. If it is determined that the rate of variance exceeds a predetermined threshold, then the data packet in process may be deemed invalid. The FIFO buffer stores all or a subset of this data, including any associated validity or error flags.

Thereafter, the data processing is performed on the stored data to determine, for example, the respective glucose level estimation or calculation. That is, the stored data in the FIFO buffer, in one embodiment, is processed to reduce unwanted variation in signal measurements due to noise or time delay, among others. In one aspect, when the rate of change or a certainty measure of the rate of change of the data stored in the FIFO buffer is within a predetermined limit, the glucose measurements are filtered over a 15 minute period. On the other hand, if it is determined that the rate of change or the certainty measure of the rate of change is greater than the predetermined limit, a more responsive 2 minute filtering is performed. In one aspect, the filtering is performed for each 60 second glucose data. In this manner, in one embodiment, a rate variance filter is provided that may be configured to smooth out the variation in the glucose measurement when the glucose level is relatively stable, and further, that can respond quickly when the glucose level is changing rapidly. The rate variance filter may be implemented in firmware as an FIR filter which is stable and easy to implement in integer-based firmware, for example, implemented in fixed point math processor.

In one embodiment, for each 60 second glucose data received, two filtered values and two additional parameters are determined. That is, using an FIR filter, for example, a weighted average for a 15 minute filtered average glucose value and a 2 minute average filtered glucose value are determined. In addition, a rate of change based on 15 minutes of data as well as a standard deviation is determined. To determine the final filtered glucose value for output and/or display to the user, a weighted average of the two determined filtered glucose values is determined, where when the rate of change of the glucose values is above a predetermined threshold (high), then weighting is configured to tend towards the 2 minute filtered value, while when the uncertainty is high, the weighting tends towards the 15 minute filtered value. In this manner, when the rate of change is high, the 2 minute filtered value is weighted more heavily (as the 15 minute filtered average value potentially introduces lag, which at higher rates of change, likely results in large error).

Referring back, during the calibration routine, in one embodiment, when the discrete blood glucose value (or reference glucose value) is received to calibrate the analyte related data from the sensor 101 (FIG. 1), the processing unit of the receiver/monitor unit 104/106 is configured to retrieve from the FIFO buffer two of the last five valid transmitter data packet that does not include any data quality flags associated with the respective data packets. In this manner, in one aspect, calibration validation check may be performed when the blood glucose value is provided to the receiver/monitor unit 104/106 determined using, for example, a blood glucose meter. In the event that two valid data packets from the last five data packets cannot be determined, the receiver/monitor unit 104/106 is configured to alarm or notify the user, and the calibration routine is terminated.

On the other hand, if the calibration validation check is successful, the sensitivity associated with the sensor 101 (FIG. 1) is determined, and its range verified. In one aspect, if the sensitivity range check fails, again, the receiver/monitor unit 104/106 may be configured to alarm or otherwise notify the user and terminate the calibration routine. Otherwise, the determined sensitivity is used for subsequent glucose data measurement and processing (until a subsequent calibration is performed).

In one aspect, when calibration is required, the underlying conditions for performing calibration are verified or evaluated to determine whether the conditions associated with the calibration routine is appropriate, and the resulting determination (whether the conditions are appropriate or not) is indicated to the user. For example, the determination of whether the underlying one or more conditions (pre-calibration conditions) are appropriate for the calibration routine may include adequate sensor data availability and validity for sensitivity determination, adequate sensor data availability and validity for rate of change determination, assessment of the rate of change based on a predetermined threshold level, determination of the higher order sensor data variation estimate below a predetermined threshold level, the elapsed time since the sensor insertion exceeding a predetermined time period, the temperature associated with the sensor data within a predefined range, suitability of the calibration routine timing, and the like.

Based on the result of the pre-calibration processing described above, for example, in one embodiment, the user is notified of the outcome of the pre-calibration condition determination. For example, in one aspect, the user may be provided with a "wait" icon displayed on the user interface of the receiver/monitor unit 104/106 (FIG. 1) when calibration is necessary but it has been determined that the conditions associated with the calibration routine are not appropriate. Thereafter, when the one or more underlying conditions associated with the calibration routine changes, and thus the calibration may be performed, the "wait" icon displayed may be changed into another icon or visual display (such as a blood drop icon, for example), or any other suitable user notification output. For example, the notification associated with the calibration, the determination of the underlying conditions associated with the calibration routine and the like may be provided using one or more graphical, text, audible and tactile output.

In one aspect, the sensor 101 (FIG. 1) may require a predetermined number of baseline calibrations during its use. For a five day operational lifetime of a sensor, four calibrations may be required at different times during the five day period. More specifically, in one embodiment, the user may be prompted to perform the scheduled calibrations based on a predetermined calibration schedule.

For each sensor implant period, which is for a predetermined time (for example, 3 days, 5 days or 7 days), baseline calibrations are required at predefined times which can be determined in different ways. The first baseline calibration time may be a predefined elapsed time relative to sensor insertion confirmation. In one embodiment, the two or more following baseline calibration request times are each based on predefined elapsed time periods since the last successful baseline calibration. For instance, in the embodiment in which the initial baseline request is made at 10 hours since insertion, baseline calibration requests are made for the second, third and fourth baseline calibrations 2, 12 and 48 hours since the last successful baseline calibration, respectively.

In a further aspect, the scheduled calibration timing may be relative to the prior calibration time periods, starting with the initial sensor positioning. That is, after the initial transcutaneous positioning of the sensor 101 (FIG. 1) and the scheduled time period has elapsed to allow the sensor 101 to reach a certain stability point, the user may be prompted to perform the first baseline calibration as described above (for example, at the 10th hour since the initial sensor placement).

In the case when the user waits until the 11th hour to perform the initial baseline calibration, the second scheduled calibration at the 12th hour, for example, may be performed at the 13th hour (so that the two hour spacing between the two calibrations are maintained, and the second calibration timing is based on the timing of the first successful baseline calibration performed. In an alternate embodiment, each scheduled calibration time period may be based on the timing of the initial sensor positioning. That is, rather than determining the appropriate subsequent calibration time periods based on the prior calibration performed, the timing of the scheduled calibration time periods may be made to be absolute and based from the time of the initial sensor placement.

Furthermore, in one aspect, when the scheduled calibration is not performed at the scheduled time periods, the glucose values may nevertheless be determined based on the sensor data for display to the user for a limited time period (for example, for no more than two hours from when the scheduled calibration time period is reached). In this manner, a calibration time window may be established or provided to the user with flexibility in performing the scheduled calibration and during which the glucose values are determined for output display to the user, for example. In one aspect, if within the calibration time window for the scheduled calibrations are not performed, the glucose values may be deemed in error, and thus not provided to the user or determined until the calibration is performed.

For example, after the initial successful baseline calibration at the 10th hour (for example, or at any other suitable scheduled initial baseline calibration time), glucose values are displayed or output to the user and stored in a memory. Thereafter, at the next scheduled calibration time period (For example, at the 12th hour), the user may be prompted to perform the second calibration. If the user does not perform the second calibration, a grace period of two hours, for example, is provided during which valid glucose values and alarms are provided to the user (for example, on the display unit of the receiver/monitor unit 104/106) based on the prior calibration parameters (for example, the initial baseline calibration performed at the 10th hour). However, if the second calibration is still not performed after the grace period, in one aspect, no additional glucose values are provided to user until the scheduled calibration is performed. Additionally, in one aspect, the user is notified that glucose values and alarms are no longer provided.

In still another aspect, the user may supplement the scheduled calibrations, and perform manual calibration based on the information that the user has received. For example, in the case that the user determines that the calibration performed and determined to be successful by the receiver/monitor unit 104/106, for example, is not sufficiently accurate, rather than replacing the sensor, the user may recalibrate the sensor even if the scheduled calibration time has not reached. For example, based on a blood glucose test result, if the determined blood glucose level is not close to or within an acceptable range as compared to the sensor data, the user may determine that additional calibration may be needed.

In the case where the scheduled calibration is not performed, in one embodiment, the glucose value determination for user display or output (on the receiver/monitor unit 104/106, for example) based on the received sensor data may be disabled after a predetermined time period has lapsed. In another embodiment, the two or more following baseline calibration request times are each based on predefined elapsed time periods since insertion confirmation. For instance, in one embodiment, when the initial baseline request is made at 1 hour since sensor insertion, the subsequent baseline calibration requests may be made at 1.5, 10, 24, 72 and 120 hours, respectively since the last successful baseline calibration. Alternatively, the second baseline calibration request time may be relative to the first successful baseline calibration, with the subsequent calibration time periods determined relative to the sensor insertion confirmation.

Furthermore, if the actual performed calibration is delayed beyond a predefined calibration prompt time, it is possible that the next scheduled baseline calibration request could occur prior to the previous baseline calibration actually occurring. In this case, the earlier baseline calibration request may be ignored. Within the scope of the present invention, other combinations of the timing approaches, relative to successful baseline calibration or relative to sensor insertion, are contemplated.

When a calibration routine fails, the receiver/monitor unit 104/106 in one embodiment displays a notification or a message indicating to the user that the calibration has failed. The displayed message would indicate that the user should repeat the reference glucose measurement immediately or after a predetermined time period has elapsed or after mitigating some circumstance that is preventing calibration, such as skin temperature being out of range, for example. The indication or message presented to the user may depend on the reason for the calibration routine failure and/or other conditions. For instance, if the calibration failed because there was an error in the reference glucose reading, then the indication presented to the user would be to repeat the calibration immediately. If the calibration failed because the reference glucose reading was out of range, the indication would be to repeat the calibration in an hour, allowing time for the glucose level to fall back into the predetermined range. If the calibration failed because the sensitivity was out of range, the indication would be to repeat the calibration in a half an hour (or some other suitable time period) to allow sufficient time for the sensitivity to recover.

In still another embodiment, after a calibration failure, when the indication is to attempt calibration at a later time, the receiver/monitor 104/106 may be configured to provide an alarm at this later time to remind the user to perform the calibration.

For the initial calibration, a timer may be set so that a minimum time elapses before calibration is attempted. In one embodiment, the time from sensor insertion confirmation to the first calibration request is approximately 10 hours, for example, to avoid or minimize sensor sensitivity attenuation during this time period.

Referring back, optimal sensitivity accuracy accounts for error sources represented in each blood glucose value calibration and the potential sensitivity drift. Accordingly, using a weighted average of the two most recent blood glucose values used for calibration, the sensitivity accuracy may be optimized. For example, in one embodiment, a weighted average of the two most recent blood glucose values used for calibration may be used to determine a composite sensitivity determination to improve accuracy and reduce calibration errors. In this aspect, earlier blood glucose values used for calibration are discarded to accommodate for sensitivity drift. In one embodiment, the number of blood glucose values used for determining the weighted average, and also, the weighting itself may be varied using one or more approaches including, for example, a time based technique.

For example, for each sensor calibration routine, the sensitivity derived from the blood glucose value from the current blood glucose test and the stored sensitivity value associated with the most recent prior stored blood glucose value may be used to determine a weighted average value that is optimized for accuracy. Within the scope of the present invention, as discussed above, the weighting routine may be time based such that if the earlier stored blood glucose value used for prior calibration is greater than a predetermined number of hours, then the weighting value assigned to the earlier stored blood glucose may be less heavy, and a more significant weighting value may be given to the current blood glucose value to determine the composite sensitivity value.

In one embodiment, a lookup table may be provided for determining the composite sensitivity determination based on a variable weighting average which provides a non-linear correction to reduce errors and improve accuracy of the sensor sensitivity.

Periodically, when a calibration is performed, the result is substantially wrong and can be deemed an outlier. When a previous sensitivity estimate (referred to hereafter as the "original sensitivity estimate") is available to the receiver/monitor unit 104/106 (FIG. 1) from one or more previous calibrations or from some other source such as a sensor code entered by the user, the sensitivity from the present calibration can be compared to determine if it is a likely outlier. During the outlier check routine performed by the receiver/monitor unit 104/106, for example, it is determined whether the sensitivity difference between two successive calibrations are within a predetermined acceptable range. If it is determined that the difference is within the predetermined range, then the present sensitivity is accepted (that is, not deemed an outlier) and a new composite sensitivity value is determined based on a weighted average of the two sensitivity values. As discussed above, the weighted average may include a time based function or any other suitable discrete weighting parameters.

If on the other hand, the difference between the two sensitivities is determined to be outside of the predetermined acceptable range, then the second (more recent) sensitivity value is considered to be a potential outlier (for example, due to sensitivity attenuation or due to bad or erroneous blood glucose value), and the user is prompted to perform another fingerstick testing to enter a new blood glucose value (for example, using a blood glucose meter).

If the difference between the second current sensitivity associated with the new blood glucose value and the prior sensitivity (the one that is a potential outlier) is determined to be outside the predetermined acceptable range, then the second current sensitivity is compared to the original sensitivity estimate. If the difference is within a predetermined acceptable range, then it is determined that the potential outlier sensitivity was indeed an outlier and the composite sensitivity is determined based the second current sensitivity value and the original sensitivity.

On the other hand, when the second current sensitivity value is determined to be within the predetermined acceptable range of the prior sensitivity value (the one that is a potential outlier), then it is determined that a sensitivity shift, rather than an outlier, has occurred prior to the time of the prior sensitivity. Accordingly, the composite sensitivity may be determined based, in this case, on the first and second current sensitivity values.

If, for example, the second current sensitivity value is determined to be outside the predetermined range of both of the two successive sensitivities described above, then the user in one embodiment is prompted to perform yet another blood glucose test to input another current blood glucose value, and the outlier check routine described above is repeated.

Referring to the Figures, during the period of use, as discussed above, the sensor 101 (FIG. 1) is periodically calibrated at predetermined time intervals. In one aspect, after the second baseline calibration (for example, at 12th hour of sensor 101 transcutaneously positioned in fluid contact with the user's analyte), sensor sensitivity stability verifications may be performed to determine whether, for example, additional stability calibrations may be necessary before the third baseline calibration is due. In one aspect, the sensitivity stability verification may be performed after the outlier checks as described above is performed and prior to the third scheduled baseline calibration at the 24th hour (or at another suitable scheduled time period).

That is, the sensor sensitivity may be attenuated (e.g., ESA) early in the life of the positioned sensor 101 (FIG. 1), and if not sufficiently dissipated by the time of the first baseline calibration, for example, at the 10th hour (or later), and even by the time of the second calibration at the 12th hour. As such, in one aspect, a relative difference between the two sensitivities associated with the two calibrations is determined. If the determined relative difference is within a predefined threshold or range (for example, approximately 26% variation), then it is determined that the sufficient stability point has been reached. On the other hand, if the relative difference determined is beyond the predefined threshold, then the user is prompted to perform an additional calibration at a timed interval (for example, at each subsequent 2 hour period), when the stability check may be repeated. This may be repeated for each two hour interval, for example, until acceptable stability point has been reached, or alternatively, until the time period for the third baseline calibration is reached, for example, at the 24th hour of sensor 101 (FIG. 1) use.

In this manner, in one aspect, the stability verification may be monitored as the sensitivity attenuation is dissipating over a given time period. While the description above is provided with particular time periods for baseline calibrations and additional calibration prompts for stability checks, for example, within the scope of the present invention, other time periods or calibration schedules including stability verifications may be used. In addition, other suitable predefined threshold or range of the relative sensitivity difference to determine acceptable attenuation dissipation other than approximately 26% may be used. Moreover, as discussed above, the predetermined calibration schedule for each sensor 101 (FIG. 1) may be modified from the example provided above, based on, for example, the system design and/or sensor 101 (FIG. 1) configuration.

Furthermore, in one aspect, reference glucose readings taken for other reasons (for instance, to evaluate whether the sensitivity has been attenuated) may be used for calibration, even when the baseline calibration timers are such that baseline calibration may not be required.

As the sensitivity value of a given sensor tends to stabilize over time, a manual user initiated calibration later in the sensor's life may provide improved accuracy in the determined glucose values, as compared to the values based on calibrations performed in accordance with the prescribed or predetermined calibration schedule. Accordingly, in one aspect, additional manual calibrations may be performed in addition to the calibrations based on the predetermined calibration schedule.

In a further aspect, user notification functions may be programmed in the receiver/monitor unit 104/106, or in the transmitter unit 102 (FIG. 1) to notify the user of initial conditions associated with the sensor 101 (FIG. 1) performance or integrity. That is, visual, auditory, and/or vibratory alarms or alerts may be configured to be triggered when conditions related to the performance of the sensor are detected. For example, during the initial one hour period (or some other suitable time period) from the sensor insertion, in the case where data quality flags/conditions (described above) are detected, or in the case where low or no signal from the sensor is detected from a given period of time, an associated alarm or notification may be initiated or triggered to notify the user to verify the sensor position, the sensor contacts with the transmitter unit 102 (FIG. 1), or alternatively, to replace the sensor with a new sensor. In this manner, rather than waiting a longer period until the acceptable sensor stability point has been reached, the user may be provided at an early stage during the sensor usage that the positioned sensor may be defective or has failed.

In addition, other detected conditions related to the performance of the sensor, calibration, or detected errors associated with the glucose value determination, may be provided to the user using one or more alarm or alert features. For example, when the scheduled calibration has not been timely performed, and the grace period as described above has expired, in one embodiment, the glucose value is not processed for display or output to the user anymore. In this case, an alarm or alert notifying the user that the glucose value cannot be calculated is provided so that the user may timely take corrective actions such as performing the scheduled calibration. In addition, when other parameters that are monitored such as the temperature, sensor data, and other variables that are used to determine the glucose value, include error or otherwise is deemed to be corrupt, the user may be notified that the associated glucose value cannot be determined, so that the user may take corrective actions such as, for example, replacing the sensor, verifying the contacts between the sensor and the transmitter unit, and the like.

In this manner, in one embodiment, there is provided an alarm or notification function that detects or monitors one or more conditions associated with the glucose value determination, and notifies the user of the same when such condition is detected. Since the alarms or notifications associated with the glucose levels (such as, for example, alarms associated with potential hyperglycemic, hypoglycemic, or programmed trend or rate of change glucose level conditions) will be inactive if the underlying glucose values cannot be determined, by providing a timely notification or alarm to the user that the glucose value cannot be determined, the user can determine or be prompted/notified that these alarms associated with glucose levels are inactive.

In one aspect of the present invention, glucose trend information may be determined and provided to the user, for example, on the receiver/monitor unit 104/106. For example, trend information in one aspect is based on the prior monitored glucose levels. When calibration is performed, the scaling used to determine the glucose levels may change. If the scaling for the prior glucose data (for example, one minute prior) is not changed, then in one aspect, the trend determination may be more error prone. Accordingly, in one aspect, to determine accurate and improved trend determination, the glucose level determination is performed retrospectively for a 15 minute time interval based on the current glucose data when each successive glucose level is determined.

That is, in one aspect, with each minute determination of the real time glucose level, to determine the associated glucose trend information, the stored past 15 minute data associated with the determined glucose level is retrieved, including the current glucose level. In this manner, the buffered prior glucose levels may be updated with new calibration to improve accuracy of the glucose trend information.

In one aspect, the glucose trend information is determined based on the past 15 minutes (or some other predetermined time interval) of glucose data including, for example, the current calibration parameter such as current sensitivity. Thereafter, when the next glucose data is received (at the next minute or based on some other timed interval), a new sensitivity is determined based on the new data point associated with the new glucose data. Also, the trend information may be determined based on the new glucose data and the past 14 minutes of glucose data (to total 15 minutes of glucose data). It is to be noted that while the trend information is determined based on 15 minutes of data as described above, within the scope of the present invention, other time intervals may be used to determine the trend information, including, for example, 30 minutes of glucose data, 10 minutes of glucose data, 20 minutes of glucose data, or any other appropriate time intervals to attain an accurate estimation of the glucose trend information.

In this manner, in one aspect of the present invention, the trend information for the historical glucose information may be updated based on each new glucose data received, retrospectively, based on the new or current glucose level information, and the prior 14 glucose data points (or other suitable number of past glucose level information). In another aspect, the trend information may be updated based on a select number of recent glucose level information such that, it is updated periodically based on a predetermined number of determined glucose level information for display or output to the user.

In still another aspect, in wireless communication systems such as the data monitoring and management system 100 (FIG. 1), the devices or components intended for wireless communication may periodically be out of communication range. For example, the receiver/monitor unit 104/106 may be placed out of the RF communication range of the transmitter unit 102 (FIG. 1). In such cases, the transmitted data packet from the transmitter unit 102 may not be received by the receiver/monitor unit 104/106, or due to the weak signaling between the devices, the received data may be invalid or corrupt. In one aspect, the transmitter unit 102 (FIG. 1) may be configured to transmit the most recent 3 minutes of data in each data packet to the receiver/monitor unit 104/106 in order to help minimize the impact of dropped packets. Other time periods of data may be contemplated. The receiver/monitor unit 104/106 may be configured to account for the missing data by identifying that data was not received at the time expected and processing the data as if it were received but invalid. When a data packet is eventually received, and previous data was missed, the receiver/monitor unit retrieves the previous data and updates the FIFO buffer for subsequent glucose calculations, trend calculations and/or filtering operations.

In cases where there are missing data points associated with the periodically monitored glucose levels, the trend information (and filtered glucose) may be nevertheless determined. The trend information is determined based on a predetermined time period of past or prior glucose data points (for example, the past 15 minutes of glucose data).

In one aspect, even if there is a certain number of glucose data points within the 15 minute time frame that may be either not received by the receiver/monitor unit 104/106, or alternatively be corrupt or otherwise invalid due to, for example, weakness in the communication link, the trend information may be determined. For example, given the 15 minutes of glucose data, if up to 3 of the 15 data points are not received or otherwise corrupt, the receiver/monitor unit 104/106 may still determine the glucose trend information based on the other 12 glucose data points that are received and considered to be valid. As such, the features or aspects of the analyte monitoring system which are associated with the determined trend information may continue to function or operate as programmed.

That is, the projected alarms or alerts programmed into the receiver/monitor unit 104/106, or any other alarm conditions associated with the detection of impending hyperglycemia, impending hypoglycemia, hyperglycemic condition or hypoglycemic condition (or any other alarm or notification conditions) may continue to operate as programmed even when there are a predetermined number or less of glucose data points. However, if and when the number of missing glucose data points exceed the tolerance threshold so as to accurately estimate or determine, for example, the glucose trend information, or any other associated alarm conditions, the display or output of the associated glucose trend information or the alarm conditions may be disabled.

For example, in one aspect, the glucose trend information and the rate of change of the glucose level (which is used to determine the trend information) may be based on 15 minute data (or data based on any other suitable time period) of the monitored glucose levels, where a predetermined number of missing data points within the 15 minutes may be tolerated. Moreover, using least squares approach, the rate of change of the monitored glucose level may be determined to estimate the trend, where the monitored valid glucose data are not evenly spaced in time. In this approach, the least squares approach may provide an uncertainty measure of the rate of change of the monitored glucose level. The uncertainly measure, in turn, may be partially dependent upon the number of valid data points available.

Indeed, using the approaches described above, the trend information or the rate of change of the glucose level may be estimated or determined without the need to determine which data point or glucose level is tolerable, and which data point is not tolerable. For example, in one embodiment, the glucose data for each minute including the missing date is retrieved for a predetermined time period (for example, 15 minute time period). Thereafter, least squares technique is applied to the 15 minute data points. Based on the least squares (or any other appropriate) technique, the uncertainly or a probability of potential variance or error of the rate of glucose level change is determined. For example, the rate of change may be determined to be approximately 1.5 mg/dL/minute+/−0.1 mg/dL/ minute. In such a case, the 0.1 mg/dL/minute may represent the uncertainly information discussed above, and may be higher or lower depending upon the number of data points in the 15 minutes of data that are missing or corrupt.

In this manner, in one aspect, the glucose trend information and/or the rate of change of monitored glucose level may be determined based on a predefined number of past monitored glucose level data points, even when a subset of the predefined number of past monitored glucose level data points are missing or otherwise determined to be corrupt. On the other hand, when the number of past glucose level data points based on which the glucose trend information is determined, exceeds the tolerance or acceptance level, for example, the display or output of the glucose trend information may be disabled. Additionally, in a further aspect, if it is determined that the underlying data points associated with the monitored glucose level based on which the trend information is determined, includes uncertainly or error factor that exceeds the tolerance level (for example, when there are more than a predetermined number of data points which deviate from a predefined level), the receiver/monitor unit 104/106, for example, may be configured to disable or disallow the display or output of the glucose trend information.

For example, when the 15 minute glucose data including the current glucose level as well as the past 14 minutes of glucose level data is to be displayed or output to the user, and the determined variance of the 15 data points exceeds a preset threshold level (for example, 3.0), the glucose trend information display function may be disabled. In one aspect, the variance may be determined based on the square function of the standard deviation of the 15 data points. In one aspect, this approach may be performed substantially on a real time basis for each minute glucose data. Accordingly, as discussed above, the glucose trend information may be output or displayed substantially in real time, and based on each new glucose data point received from the sensor/transmitter unit.

Additionally, when it is determined that the 15 data points (or any other suitable number of data points for determining glucose trend information, for example), deviate beyond a predetermined tolerance range, in one aspect, the 15 minute data may be deemed error prone or inaccurate. In this case, rather than outputting or displaying glucose trend information that may be erroneous, the receiver/monitor unit 104/106 may be configured to disable the output or display function related to the output or display of the determined glucose trend information. The same may apply to the output or display of projected alarms whose estimates may be based, in part, on the determined trend information. Accordingly, in one aspect, there may be instances when the projected alarm feature may be temporarily disabled where the underlying monitored glucose data points are considered to include more than an acceptable level of uncertainly or error.

In a further aspect, it is desired to determine an estimate of sensor sensitivity, and/or a range of acceptable or reasonable sensitivity. For example, during determination or verification of the glucose rate of change prior to calibration, the estimated sensor sensitivity information is necessary, for example, to determine whether the rate of change is within or below an acceptable threshold level, and/or further, within a desired range. Moreover, when determining whether the sensor sensitivity is within an acceptable or reasonable level, it may be necessary to ascertain a range of reasonable or acceptable sensitivity—for example, a verification range for the sensitivity value for a given sensor or batch of sensors.

Accordingly, in one aspect, during sensor manufacturing process, a predetermined number of sensor samples (for example, 16 samples) may be evaluated from each manufacturing lot of sensors (which may include, for example, approximately 500 sensors) and the nominal sensitivity for each lot (based, for example, on a mean calculation) may be determined. For example, during the manufacturing process, the predetermined number of sensors (for example, 16 sensors) is sampled, and the sensitivity of each sampled sensor is measured in vitro. Thereafter, a mean sensitivity may be determined as an average value of the 16 sampled sensor's measured sensitivity, and thereafter, the corresponding sensor code is determined where the determined mean sensitivity falls within the preassigned sensitivity range. Based on the determined sensor code, the sensor packaging is labeled with the sensor code.

For example, each sensor code value (e.g., 105, 106, 107 or any suitable predetermined number or code) may be preassigned a sensitivity range (For example, code 105: S1-S2, code 106: S2-S3, and code 107: S3-S4), where each sensitivity range (e.g., S1-S2, or S2-S3, or S3-S4) is approximately over a 10 percent increment (for example, S1 is approximately 90% of S2). Also, each sensor code (e.g., 105, 106, 107 etc) is assigned a nominal sensitivity value (Sn) that is within the respective preassigned sensitivity range.

Referring back, when the user inserts the sensor or positions the sensor transcutaneously in place, the receiver/monitor unit 104/106 in one embodiment prompts the user to enter the associated sensor code. When the user enters the sensor code (as derived from the sensor packing label discussed above), the receiver/monitor unit 104/106 is configured to retrieve or look up the nominal sensitivity associated with the user input sensor code (and the nominal sensitivity which falls within the preassigned sensitivity range associated with that sensor code, as described above). Thereafter, the receiver/monitor unit 104/106 may be configured to use the sensor code in performing associates routines such as glucose rate of change verification, data quality checks discussed above, and/or sensor sensitivity range acceptability or confirmation.

In a further aspect, the sensor codes may be associated with a coefficient of variation of the predetermined number of sampled sensors discussed above in addition to using the mean value determined as discussed above. In one embodiment, the coefficient of variation may be determined from the predetermined number of sampled sensors during the manufacturing process. In addition, the mean response time of the sampled sensors may be used by separately measuring the predetermined number of sampled sensors which may be used for lag correction adjustments and the like.

In this manner, in one aspect, the manufacturing process control described above ensures that the coefficient of variation of the sampled sensors is within a threshold value. That is, the value of the nominal sensitivity is used to determine a sensor code, selected or looked up from a predetermined table, and that is assigned to the sensors from the respective sensor lot in manufacturing. The user then enters the sensor code into the receiver/monitor unit that uses the sensor code to determine the glucose rate of change for purposes of data quality checking, for example, and also to determine validity or reasonableness of the sensitivity that is determined.

Figure 11:
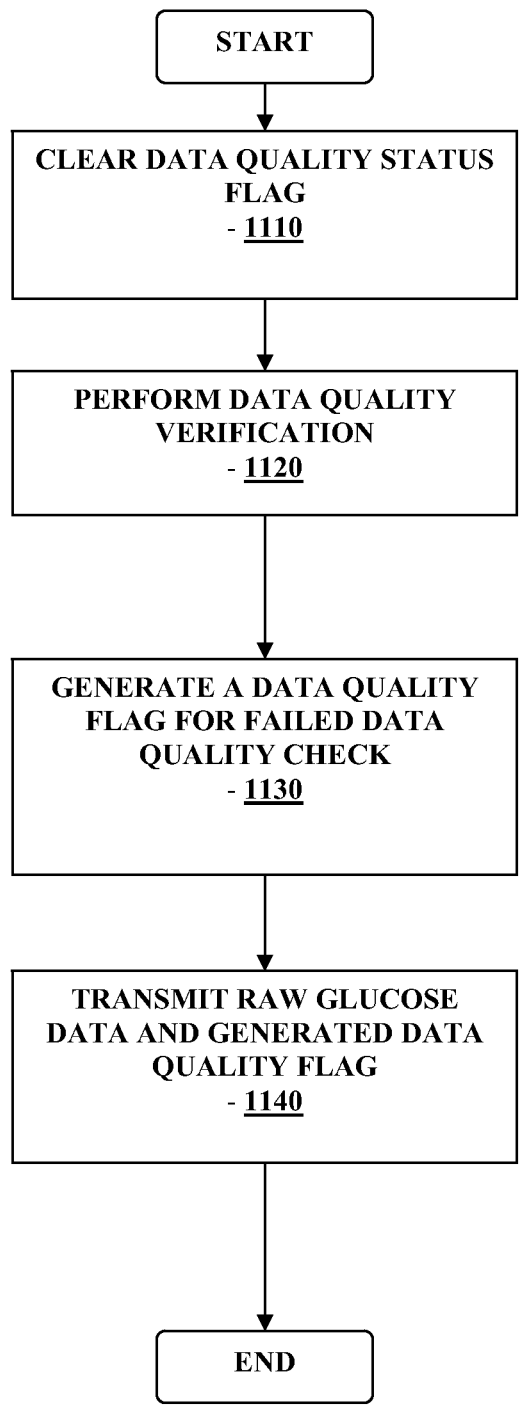
FIG. 11 is a flowchart illustrating a data quality verification routine in accordance with one embodiment of the present invention.

FIG. 11 is a flowchart illustrating a data quality verification routine in accordance with one embodiment of the present invention. Referring to FIG. 11, initially the data quality status flags are cleared or initialized or reset (1110). Thereafter data quality checks or verifications are performed, for example, as described above (1120). Thereafter, a data quality flag is generated and associated with the data packet when data quality check has failed (1130). Thereafter, the data packet including the raw glucose data as well as the data quality flags are transmitted (1140), for example, to the receiver/monitor unit 104/106 for further processing.

As described above, the data quality checks may be performed in the transmitter unit 102 (FIG. 1) and/or in the receiver/monitor unit 104/106 in the data monitoring and management system 100 (FIG. 1) in one aspect of the present invention.

Figure 12:
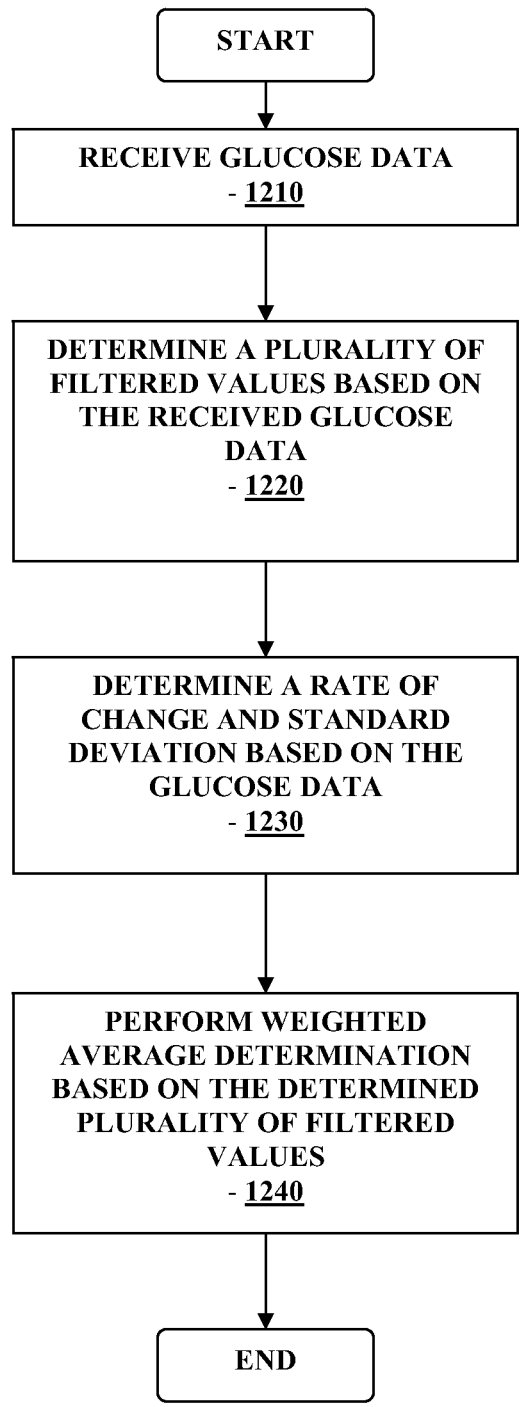
FIG. 12 is a flowchart illustrating a rate variance filtering routine in accordance with one embodiment of the present invention.

FIG. 12 is a flowchart illustrating a rate variance filtering routine in accordance with one embodiment of the present invention. Referring to FIG. 12, when glucose related data is detected or received (1210), for example, for each predetermined time intervals such as every minute, every five minutes or any other suitable time interval, a plurality of filtered values based on the received or detected unfiltered glucose values is determined (1220). For example, as discussed above, in one aspect, using, for example, an FIR filter, or based on a weighted average, a plurality of filtered values for a 15 minute and two minute glucose related data including the currently received or detected glucose related are determined. Thereafter, a rate of change of the glucose level based in part on the detected or received glucose related data is determined as well a standard deviation based on the unfiltered glucose values (1230).

Referring again to FIG. 12, a weighted average associated with the current detected or monitored glucose related data is determined based on the plurality of filtered values and the determined standard deviation as well as the rate of change of the glucose level (1240). For example, when the rate of change is determined to be greater than a predetermined threshold level, the filtered value based on the two minute data is weighted more heavily. On the other hand, when the rate of change is determined to be less than the predetermined threshold level, the filtered glucose related data includes the one of the plurality of filtered values based on the minute data which is weighted more heavily. In this manner, in one aspect, there is provided a rate variance filtering approach which may be configured to dynamically modify the weighting function or data filtering to, for example, reduce undesirable variation in glucose related signals due to factors such as noise.

Figure 13:
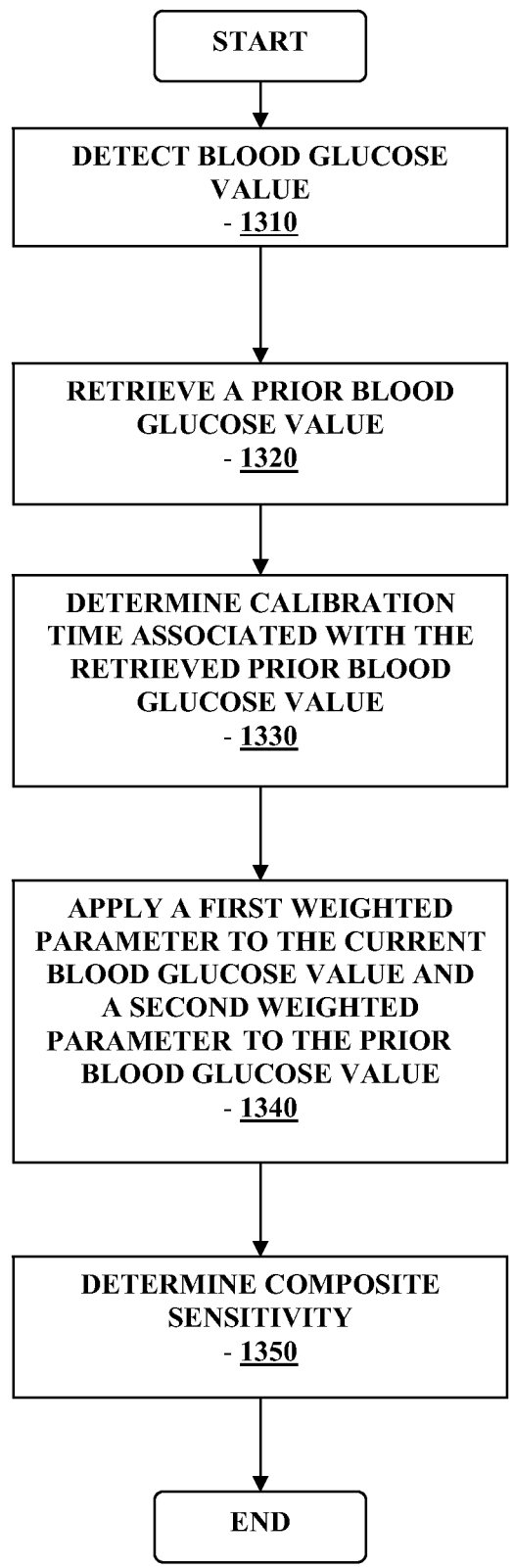
FIG. 13 is a flowchart illustrating a composite sensor sensitivity determination routine in accordance with one embodiment of the present invention.

FIG. 13 is a flowchart illustrating a composite sensor sensitivity determination routine in accordance with one embodiment of the present invention. Referring to FIG. 13, during scheduled calibration time periods or otherwise manual calibration routines to calibrate the analyte sensor, when current blood glucose value is received or detected (1310), a prior blood glucose value previously stored or otherwise received is retrieved, for example, from a storage unit such as a memory (1320). Thereafter, the calibration event time associated with the retrieved prior blood glucose value is determined or retrieved from the storage unit (1330), a first weighted parameter is applied to the current received blood glucose value, and a second weighted parameter is applied to the retrieved prior blood glucose value (1340). For example, based on the time lapsed between the calibration event associated with the retrieved blood glucose value and the current calibration event (associated with the current or received blood glucose value), the first and second weighted parameters may be modified (e.g., increased or decreased in value) to improve accuracy.

Referring back to FIG. 13, based on applying the first and the second weighted parameters to the current blood glucose value and the retrieved prior blood glucose value, a composite sensitivity associated with the analyte sensor for the current calibration event is determined (1350). For example, using a time based approach, in one embodiment, the sensitivity associated with the analyte sensor for calibration may be determined to, for example, reduce calibration errors or accommodate sensitivity drift. Alternatively, the first and the second weighted parameters may be fixed at predetermined values.

Figure 14:
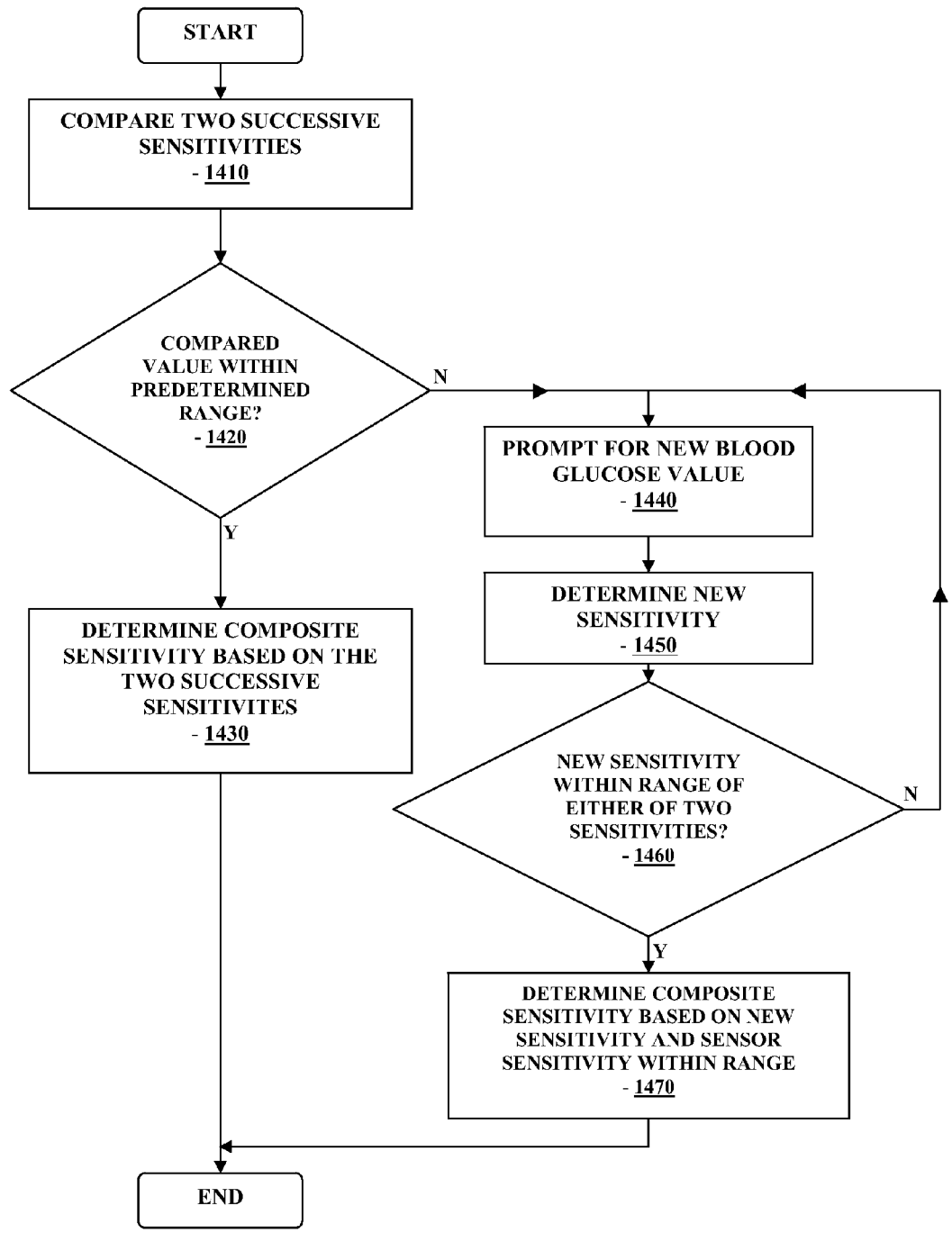
FIG. 14 is a flowchart illustrating an outlier data point verification routine in accordance with one embodiment of the present invention.

FIG. 14 is a flowchart illustrating an outlier data point verification routine in accordance with one embodiment of the present invention. Referring to FIG. 14, and as discussed in detail above, in determining composite sensitivity associated with the analyte sensor calibration, in one aspect, an outlier data point may be detected and accordingly corrected. For example, in one aspect, two successive sensitivities associated with two successive calibration events for the analyte sensor is compared (1410). If it is determined that the comparison between the two sensitivities are within a predetermined range (1420), the composite sensitivity for the current calibration of the analyte sensor is determined based on the two successive sensitivity values (1430), using, for example, the weighted approach described above.

Referring back to FIG. 14, if it is determined that the comparison of the two successive sensitivities results in the compared value being outside of the predetermined range, then the user may be prompted to enter or provide a new current blood glucose value (for example, using a blood glucose meter) (1440). Based on the new blood glucose value received, an updated or new sensitivity associated with the analyte sensor is determined (1450). Thereafter, the new or updated sensitivity determined is compared with the two prior sensitivities compared (at 1420) to determine whether the new or updated sensitivity is within a predefined range of either of the two prior sensitivities (1460). If it is determined that the new or updated sensitivity of the analyte sensor is within the predefined range of either of the two prior successive sensitivities, a composite sensitivity is determined based on the new or updated sensitivity and the one of the two prior successive sensitivities within the defined range of which the new or updated sensitivity is determined (1470). On the other hand, if it is determined that the new or updated sensitivity is not within the predefined range of either of the two prior sensitivities, then the routine repeats and prompts the user to enter a new blood glucose value (1440).

Figure 15:
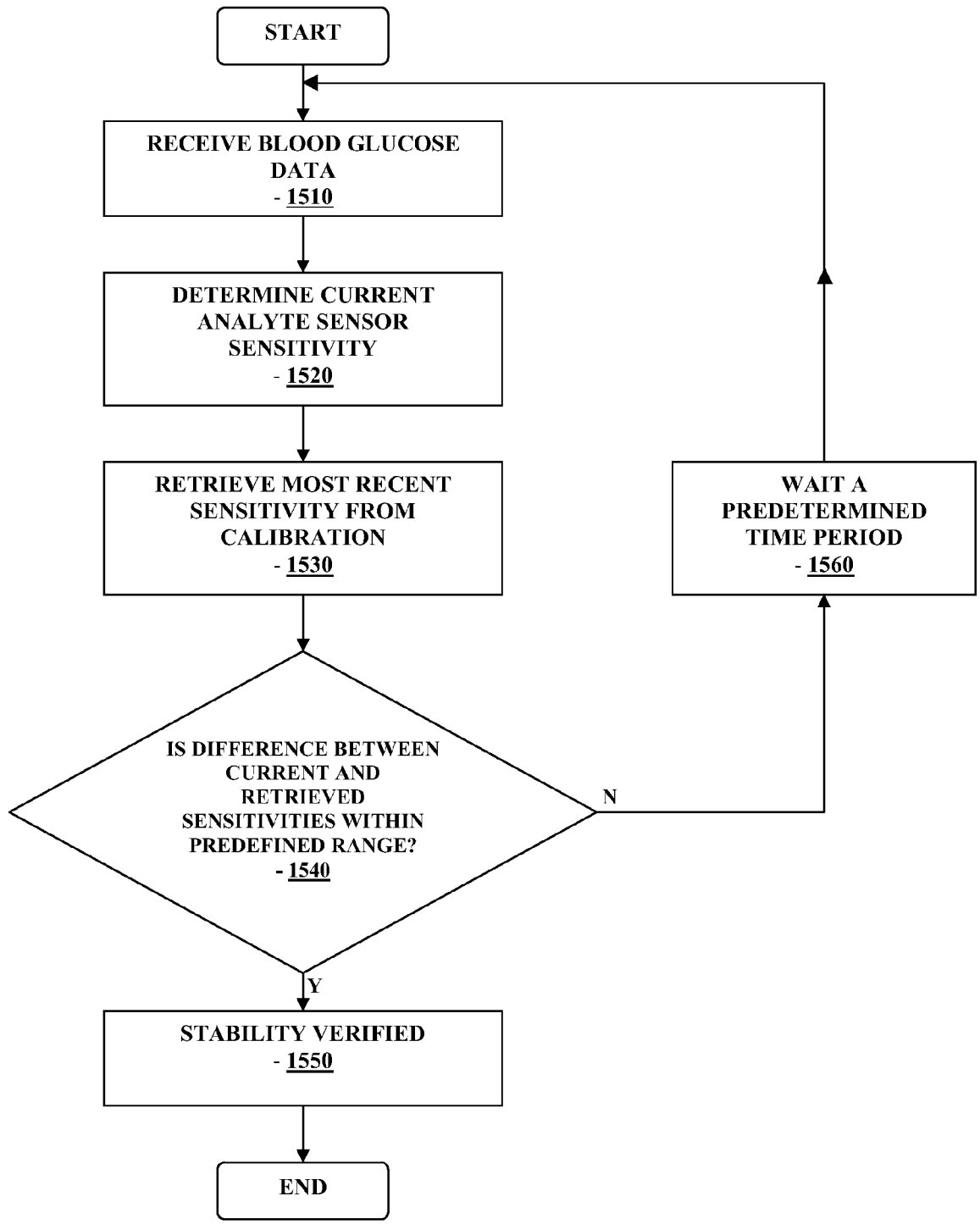
FIG. 15 is a flowchart illustrating a sensor stability verification routine in accordance with one embodiment of the present invention.

FIG. 15 is a flowchart illustrating a sensor stability verification routine in accordance with one embodiment of the present invention. Referring to FIG. 15, and as discussed above, between predetermined or scheduled baseline calibration events to calibrate the sensor, the analyte sensor sensitivity stability may be verified, to determine, for example, if additional stability calibrations may be needed prior to the subsequent scheduled baseline calibration event.

For example, referring to FIG. 15, in one embodiment, after the second baseline calibration event to calibrate the analyte sensor, the user may be prompted to provide a new blood glucose value. With the current blood glucose value received (1510), the current sensor sensitivity is determined (1520). Thereafter, the most recent stored sensor sensitivity value from prior calibration event is retrieved (for example, from a storage unit) (1530), and the determined current sensor sensitivity is compared with the retrieved stored sensor sensitivity value to determine whether the difference, if any, between the two sensitivity values are within a predefined range (1540).

Referring back to FIG. 15, if it is determined that the difference between the current and retrieved sensitivity values are within the predefined range, then the stability associated with the sensor sensitivity is confirmed (1550), and no additional calibration is required prior to the subsequent scheduled baseline calibration event. On the other hand, if it is determined that the difference between the current sensitivity and the retrieved prior sensitivity is not within the predefined range, then after a predetermined time period has lapsed (1560), the routine returns to the beginning and prompts the user to enter a new blood glucose value to perform the stability verification routine.

In this manner, in one aspect, the stability checks may be performed after the outlier check is performed, and a new composite sensitivity determined as described above. Accordingly, in one aspect, analyte sensor sensitivity may be monitored as the sensitivity attenuation is dissipating to, among others, improve accuracy of the monitored glucose data and sensor stability.

Figure 16:
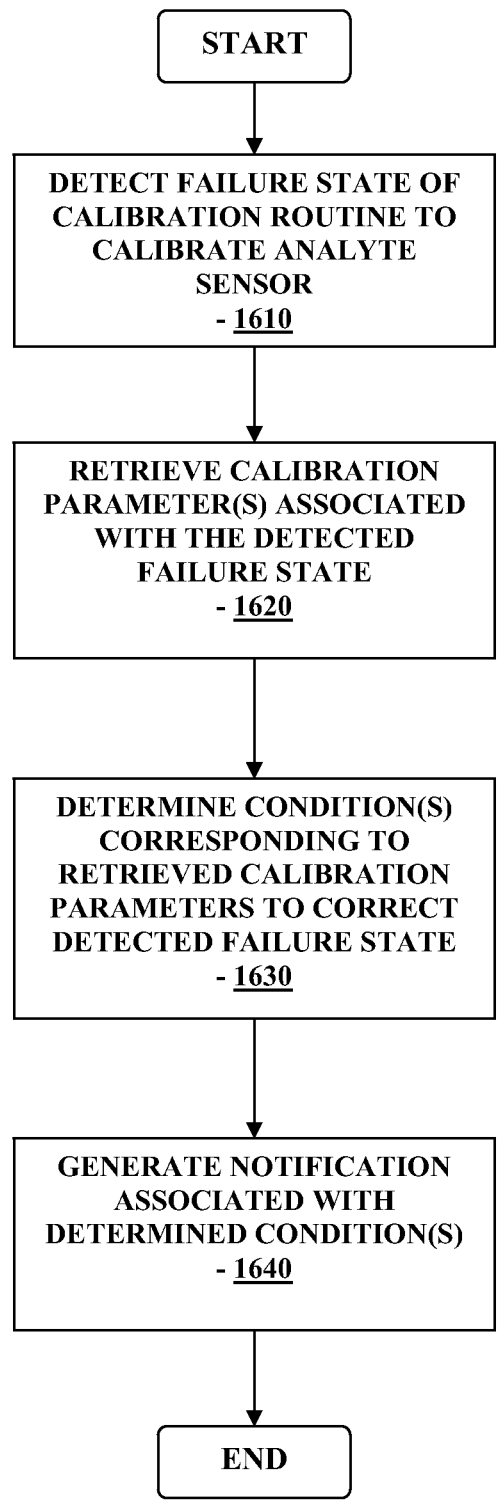
FIG. 16 is a flowchart illustrating a calibration failure state detection and/or notification routine in accordance with one embodiment of the present invention.

FIG. 16 is a flowchart illustrating a calibration failure state detection and/or notification routine in accordance with one embodiment of the present invention. Referring to FIG. 16, when a failure state of a calibration routine to calibrate an analyte sensor such as a subcutaneously positioned analyte sensor 101 (FIG. 1) is detected (1610), one or more calibration parameters associated with the calibration routine is retrieved (1620). For example, the retrieved one or more calibration related parameters may include one or more of a current sensitivity value, a predetermined number of preceding valid analyte sensor data, a valid analyte data verification, a rate of change of analyte sensor data, a predetermined number of valid analyte sensor data for sensitivity determination; a predetermined number of valid analyte sensor data for analyte sensor data rate of change determination, a temperature data associated with the analyte sensor data, a determined sensitivity data, a reference blood glucose data, or a validity indication of the reference blood glucose data.

In one aspect, the one or more calibration related parameters may be stored in a data storage unit of the receiver/monitor unit 104/106, or alternatively, may be stored in a memory device of the transmitter unit 102, for example. Additionally, the one or more calibration related parameters may be stored at a remote location such as a computer terminal or a data processing terminal 105 (FIG. 1) which may be coupled in signal communication in one or more of the transmitter unit 102 or the receiver/monitor unit 104/106.

Referring back to FIG. 16, after retrieving the one or more calibration parameters, one or more conditions corresponding to or associated with the respective one or more calibration parameters to correct the detected calibration routine failure state is determined (1630). That is, in one embodiment, when a calibration routine is initiated (based on a predetermined baseline calibration schedule or a user initiated calibration routine to calibrate the analyte sensor 101 (FIG. 1)), the parameters that are needed to perform the calibration routine is retrieved and thereafter evaluated to determine the condition associated with the one or more parameters which is associated with the calibration failure state.

For example, in one embodiment, the one or more determined conditions associated with the one or more calibration parameters that is associated with the calibration failure state may include an invalid reference blood glucose value received, a rate of change of the glucose value which deviates from a predetermined range that is established for performing the calibration routine. While these examples are described herein, in accordance with the various embodiments of the present invention, the one or more determined conditions that is associated with the one or more calibration parameters may include, for example, any invalid or not acceptable level of state of the respective calibration parameter to successfully perform the calibration routine to calibrate the analyte sensor.

Referring still again to FIG. 16, after determining the one or more conditions corresponding to the one or more retrieved calibration parameters to correct the detected calibration failure state, a notification may be generated to provide or alert the user to reenter or provide the information or data input associated with the determined one or more conditions (1640). Referring back to the example described above, if it is determined that the reference blood glucose value referenced is invalid, the notification generated and provided to the user may include a request to reenter or provide another reference blood glucose value, by, for example, prompting the user to perform another blood glucose test. If the determined condition associated with one or more calibration parameters is related to the rate of change of the analyte level that exceeds a predetermined range suitable for analyte sensor calibration, then the generated notification may include a prompt or output display to the user to wait a predetermined time period to allow the glucose level variation to settle within the acceptable range for performing the calibration routine.

In one aspect, the generated notification provided to the user may include one or more of an audible output such as an alarm, a visual output such as a static or moving icon or image on the receiver/monitor unit 104/106 (for example,), a vibratory output, or one or more combinations thereof.

In this manner, in one aspect, the user may be promptly notified of the failed calibration routine state, and further, provided with information associated with one or more corrective actions that the user may take to correct the failed calibration state to calibrate the analyte sensor.

Figure 17:
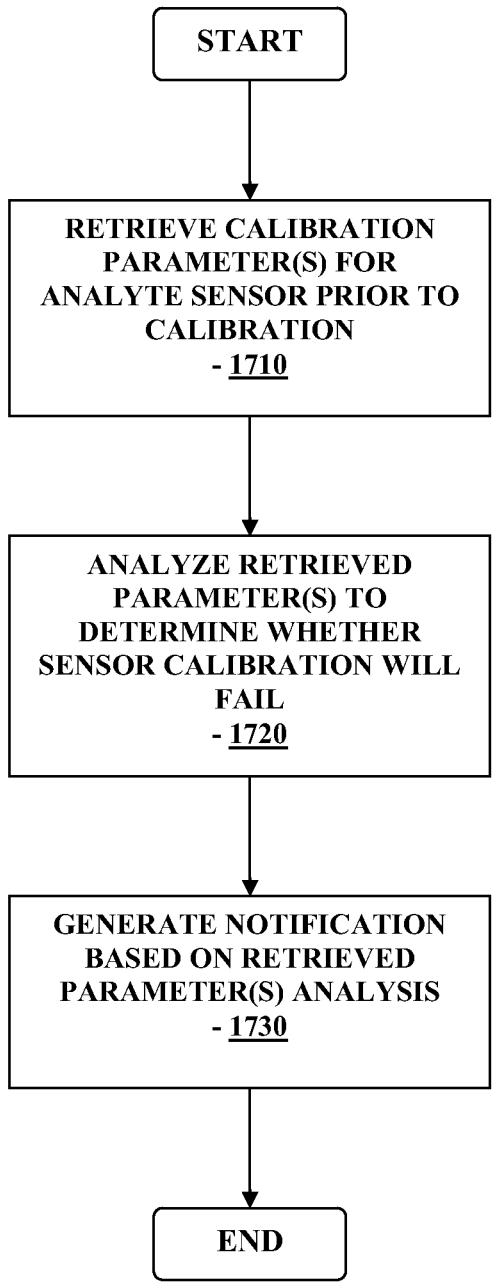
FIG. 17 is a flowchart illustrating pre-calibration analysis routine in accordance with one embodiment of the present invention.

FIG. 17 is a flowchart illustrating pre-calibration analysis routine in accordance with one embodiment of the present invention. Referring to FIG. 17, prior to performing calibration routine to calibrate an analyte sensor based, for example, on a baseline calibration schedule or on user initiated calibration routine, one or more parameters associated with the calibration routine for calibrating the analyte sensor is retrieved (1710), and the retrieved one or more parameters are analyzed to determine whether the one or more parameters are acceptable or valid to successfully perform the calibration of the analyte sensor (1720). That is, prior to the calibration routine execution, the underlying parameters are analyzed or assessed to determine whether they are valid or acceptable.

Referring to FIG. 17, after analyzing the retrieved one or more calibration related parameters to determine whether the calibration routine will be successful, a notification is generated to provide or alert the user based on the analysis of the retrieved one or more parameters associated with the calibration routine. In this manner, the user may be notified or alerted that the calibration routine will likely be unsuccessful. For example, if the user planned to perform a fingerstick test to determine and provide the blood glucose value to calibrate the analyte sensor, the analysis of the retrieved one or more calibration related parameters determining that the calibration routine will fail (for example, based on a rate of change of the analyte level that is not suitable for calibration), and the corresponding notification to the user will alert the user to not proceed with the painful fingerstick test.

In this manner, in one aspect, the user may be notified of the condition of the various parameters associated with the calibration routine, and in the case where the condition of the various calibration related parameters is not valid or suitable for performing the calibration routine, the user is notified to prevent additional steps that the user may take to complete the calibration routine which may be unnecessary. That is, in one embodiment, pre-calibration routines may be performed by one or more of the transmitter unit 102, the receiver/monitor unit 104/106, or the data processing terminal 105, for example, to determine whether the calibration routine will be successful, and when it is determined that the one or more conditions related to one or more of the calibration parameters is not suitable or valid, the user is notified.

In one aspect, the user may be notified by one or more of an audible alert, a visual output, a vibratory indication, or one or more combinations thereof. For example, an icon illustrating a blood drop which corresponds to a request or prompt to enter a blood glucose value may be displayed with a line across the icon to alert the user to not enter a blood glucose value. Alternatively, or in addition to the icon display, a text message or notification may be provided to the user with or without an audible alarm that indicates that the user should not enter a blood glucose value. In this manner, in one aspect, the user may be notified prior to the calibration routine execution, whether the calibration routine will be successful, and if not, the user will be prevented or at least notified to not take further steps or perform additional processes such as the fingerstick test, for the calibration routine.

Figure 18:
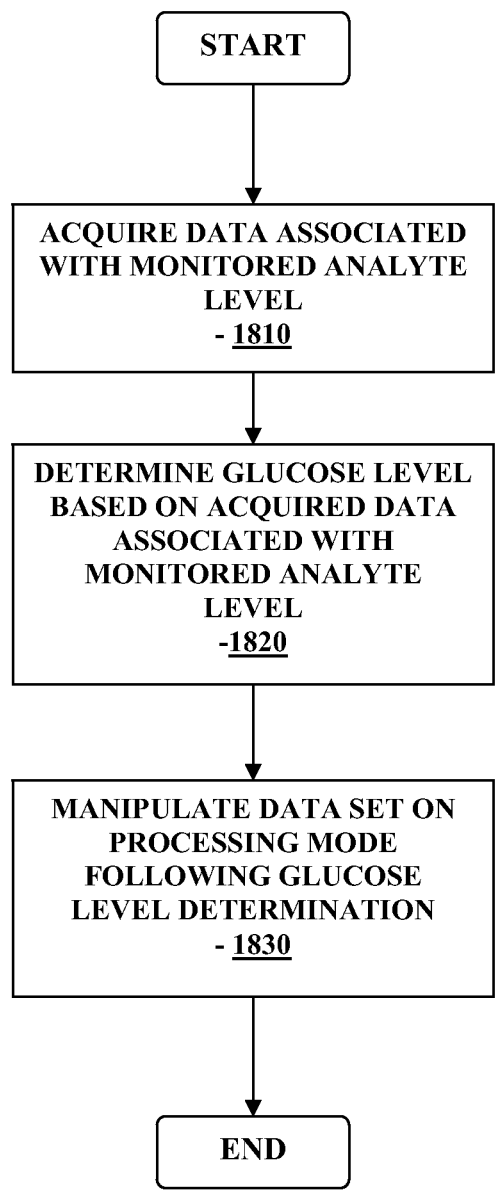
FIG. 18 is a flowchart illustrating asynchronous serial data output transmission routine in accordance with one embodiment of the present invention.

FIG. 18 is a flowchart illustrating asynchronous serial data output transmission routine in accordance with one embodiment of the present invention. Referring to FIG. 18, in one embodiment, when each analyte sensor measurement is detected or received (for example, each minute, 5 minutes, or 10 minutes, or at any other suitable intervals configured by the monitoring system) (1810), the analyte sensor measurement is processed to a corresponding glucose value (1820), and in accordance with the processing mode, the data set including for example, one or more of the glucose value, the corresponding sensor measurement, one or more calibration parameters, temperature information and the like may be manipulated (1830).

For example, in one aspect, when the processing mode is configured for asynchronous serial data output mode, the periodic sensor measurement value, the corresponding glucose level information and/or any other related data set may be manipulated or processed for real time data transmission via a serial data port, for example, in the receiver/monitor unit 104/106. In one aspect, the data set may be output substantially in real time relative to the sensor measurement over a data communication path such as a wireless or wired connection including for example, the RF communication link, a BLUETOOTH® communication link, an Infrared communication connection, a USB cable connection, or any other suitable data communication link.

In another aspect, the processing mode may be configured to display the determined glucose level substantially in real time on the display unit of the receiver/monitor unit 104/106, and also concurrently transmit the determined glucose level substantially in real time (along with other data or information associated with the determined glucose level described herein), to the data processing terminal 105 or other external devices. Alternatively, the processing mode may be configured not to display the real time glucose information, but rather, to transmit the determined glucose level and one or more other information related to the glucose level to the external device.

In this aspect, the external device (for example, the data processing terminal/infusion section 105 (FIG. 1) or any other suitable device) may be configured to query and/or obtain data from the receiver/monitor unit 104/106, where the external device may be configured to obtain the current or real time data sample from the receiver/monitor unit 104/106. More specifically, in one embodiment, when the receiver/monitor unit 104/106 receives the real time analyte related data from the transmitter unit 102 (FIG. 1) for example, the receiver/monitor unit 104/106 may be configured to automatically output or transmit, via a predetermined or configured data transmission port (or medium), the received analyte related data and/or associated data processing results.

In one embodiment, the receiver/monitor unit 104/106 may be configured to perform this operation via a serial command. Upon receipt of the command, for example, the receiver/monitor unit 104/106 may be configured to automatically send out of its serial port, for example, one or more of the following data: measured analyte sensor data, sensor temperature data, data quality detection information, error detection information, other data associated with the measured analyte sensor data, filtered and/or unfiltered glucose level determinations, intermediate glucose determinations, glucose trend information, alarm determination, system status information, for example. Alternatively, the receiver/monitor unit 104/106 may be configured to automatically transmit the data set and not in response to a command such as the serial command described above.

Furthermore, while the serial port data communication is described above, within the scope of the present disclosure, other modes of data transmission and/or communication including wireless and wired/cabled data communication are contemplated. In this manner, in one aspect, the output data from the receiver/monitor 104/106 may be placed in a buffer of predefined length (for example 2 minutes for a one minute sample rate), and when queried, outputting the last entry into the buffer. In this manner, in one aspect, monitored analyte related data may be provided to a remote device (for example, the data processing terminal/infusion section 105 (FIG. 1), automatically, for example, for further analysis and processing. In addition, the receiver/monitor unit 104/106 may be configured to communicate with other devices or systems that operate on their own time base independently.

A method in one embodiment includes detecting a failure state of a calibration routine to calibrate an analyte sensor, retrieving one or more calibration parameters associated with the detected failure state of the calibration routine, determining one or more conditions corresponding to the retrieved one or more calibration parameters to correct the detected failure state of the calibration routine, generating a notification associated with the determined one or more conditions.

The method may include outputting the generated notification associated with the determined one or more conditions, where outputting the generated notification may include outputting one or more of an audible output, a text output, a graphical output, a status screen display output, or one or more combinations thereof.

In one aspect, the method may include displaying a calibration routine failure state notification.

The generated notification may include a corrective indication to correct the detected failure state of the calibration routine, where the corrective indication may include one or more of a calibration routine repeat notification, or a calibration routine repeat after a predetermined time period notification, and further, where the predetermined time period may include one of a 30 minute time period, one hour time period, or a two hour period.

The method may also include displaying the corrective indication.

Additionally, the method may include storing the notification associated with the determined one or more conditions.

The one or more calibration parameters may include one or more of a current sensitivity value, a predetermined number of preceding valid analyte sensor data, a valid analyte data verification, a rate of change of analyte sensor data, a predetermined number of valid analyte sensor data for sensitivity determination; a predetermined number of valid analyte sensor data for analyte sensor data rate of change determination, a temperature data associated with the analyte sensor data, a determined sensitivity data, a reference blood glucose data, a validity indication of the reference blood glucose data.

The one or more conditions may include a correction factor associated with the one or more calibration parameters.

An apparatus in accordance with another embodiment includes a data storage unit, and a processing unit operatively coupled to the data storage unit configured to detect a failure state of a calibration routine to calibrate an analyte sensor, retrieve one or more calibration parameters associated with the detected failure state of the calibration routine, determine one or more conditions corresponding to the retrieved one or more calibration parameters to correct the detected failure state of the calibration routine, and generate a notification associated with the determined one or more conditions.

The apparatus may include an output unit operatively coupled to the processing unit to output the generated notification associated with the determined one or more conditions, where the output unit may be configured to output one or more of an audible output, a text output, a graphical output, a status screen display output, or one or more combinations thereof.

The apparatus in another aspect may include an output unit operatively coupled to the processing unit to display a calibration routine failure state notification.

The generated notification may include a corrective indication to correct the detected failure state of the calibration routine, where the corrective indication may include one or more of a calibration routine repeat notification, or a calibration routine repeat after a predetermined time period notification, and further, where the predetermined time period may include one of a 30 minute time period, one hour time period, or a two hour period.

The apparatus may include an output unit operatively coupled to the processing unit to display the corrective indication.

The data processing unit in another aspect may be configured to store the notification associated with the determined one or more conditions.

The one or more parameters may include one or more of a current sensitivity value, a predetermined number of preceding valid analyte sensor data, a valid analyte data verification, a rate of change of analyte sensor data, a predetermined number of valid analyte sensor data for sensitivity determination; a predetermined number of valid analyte sensor data for analyte sensor data rate of change determination, a temperature data associated with the analyte sensor data, a determined sensitivity data, a reference blood glucose data, a validity indication of the reference blood glucose data.

Also, the one or more conditions may be a correction factor associated with the one or more calibration parameters.

A method in accordance with another embodiment may include, prior to calibrating an in vivo analyte sensor, retrieving one or more parameters to calibrate the analyte sensor data, analyzing the retrieved one or more parameters to determine whether the analyte sensor data calibration will fail, and generating a notification based on the analysis of the retrieved one or more parameters.

The method may include determining a calibration time period based on a predetermined calibration schedule, where the predetermined calibration schedule may include a plurality of calibration time periods after the positioning of the analyte sensor in fluid contact with an analyte.

The plurality of calibration time periods may include two or more of 10 minutes, 30 minutes, 45 minutes, one hour, two hours, five hours, 10 hours, 12 hours, 24 hours, 48 hours or 72 hours measured from the positioning of the analyte sensor.

In another aspect, the plurality of calibration time periods may be determined based on a valid calibration procedure to calibrate the positioned analyte sensor.

The retrieved one or more parameters to calibrate the analyte sensor may include one or more of a current sensitivity value, a predetermined number of preceding valid analyte sensor data, a valid analyte data verification, a rate of change of analyte sensor data, a predetermined number of valid analyte sensor data for sensitivity determination; a predetermined number of valid analyte sensor data for analyte sensor data rate of change determination, or a temperature data associated with the analyte sensor data.

Further, the predetermined number of preceding valid analyte sensor data may include two valid analyte sensor data from the five most recent analyte sensor data determined from the analyte sensor calibration event.

In one aspect, the notification may include a request for one of a current blood glucose measurement value input, or a delayed blood glucose measurement value input.

The request in one aspect may include one or more of a text information, a graphical information, an audible information, or a combined one or more of the text, graphical or audible information to alert a user to enter a current blood glucose value.

The method in another aspect may include storing the generated notification.

Moreover, the notification may include an output signal to indicate that the one or more retrieved parameters to calibrate the analyte sensor are invalid.

In still another aspect, the notification may include an output message to prevent entering a current blood glucose value information.

When the retrieved one or more parameters to calibrate the analyte sensor are determined to be out of range for valid calibration, the method may include generating one or more notifications associated with correcting the invalid determination.

Additionally, the one or more notifications associated with correcting the invalid determination may include one or more of a skin temperature adjustment notification, a notification to control the glucose level within a predetermined range, or a notification to delay calibration until the rate of change of the glucose value is within a predetermined threshold range, where each of the one or more notifications may include an icon, an audible and/or vibratory alarm, or a status screen display.

An apparatus in accordance with still another embodiment includes a data storage unit, and a processing unit operatively coupled to the data storage unit, and configured to retrieve one or more sensor calibration parameters to calibrate an analyte sensor data prior to calibrating an in vivo analyte sensor, analyze the retrieved one or more parameters to determine whether the analyte sensor data calibration will fail, and generate a notification based on the analysis of the retrieved one or more parameters.

The processing unit may be configured to determine a calibration time period based on a predetermined calibration schedule, where the predetermined calibration schedule may include a plurality of calibration time periods after the positioning of the analyte sensor in fluid contact with an analyte.

In still a further aspect, the plurality of calibration time periods may include two or more of 10 minutes, 30 minutes, 45 minutes, one hour, two hours, five hours, 10 hours, 12 hours, 24 hours, 48 hours or 72 hours measured from the positioning of the analyte sensor.

The plurality of calibration time periods may be determined based on a valid calibration procedure to calibrate the positioned analyte sensor.

The retrieved one or more parameters to calibrate the analyte sensor may include one or more of a current sensitivity value, a predetermined number of preceding valid analyte sensor data, a valid analyte data verification, a rate of change of analyte sensor data, a predetermined number of valid analyte sensor data for sensitivity determination; a predetermined number of valid analyte sensor data for analyte sensor data rate of change determination, or a temperature data associated with the analyte sensor data, where the predetermined number of preceding valid analyte sensor data may include two valid analyte sensor data from the five most recent analyte sensor data determined from the analyte sensor calibration event.

The apparatus may also include output unit operatively coupled to the processing unit, the output unit configured to output the notification to request for one of a current blood glucose measurement value input, or a delayed blood glucose measurement value input, where the request includes one or more of a text information, a graphical information, an audible information, or a combined one or more of the text, graphical or audible information.

The processing unit may be configured to store the generated notification in the storage unit.

The notification may include an output signal to indicate that the one or more retrieved parameters to calibrate the analyte sensor is invalid.

In another aspect, the notification may include an output message to prevent entering a current blood glucose value information.

When the retrieved one or more parameters to calibrate the analyte sensor are determined to be out of range for valid calibration, the processing unit may be further configured to generate one or more notifications associated with correcting the invalid determination.

Also, the one or more notifications associated with correcting the invalid determination may include one or more of a skin temperature adjustment notification, a notification to control the glucose level within a predetermined range, or a notification to delay calibration until the rate of change of the glucose value is within a predetermined threshold range.

Moreover, each of the one or more notifications may include an icon, an audible and/or vibratory alarm, or a status screen display.

A method in accordance with still another embodiment includes acquiring data associated with a monitored analyte level, determining a glucose level based at least in part on the acquired data associated with the monitored analyte level, manipulating a data set based on a processing mode following the glucose level determination, where the processing mode includes one of a data set transmission and output display, a data set storing and output display without transmission, or a data set transmission and data set storing without output display.

The data set may be automatically transmitted following the glucose level determination.

The data set may include one or more of the monitored analyte level, temperature information associated with the monitored analyte level, a data quality information associated with the monitored analyte level, or an error detection information associated with the monitored analyte level.

Also, the data set may include one or more of a filtered glucose data, an unfiltered glucose data, glucose trend information, or glucose alarm condition determination.

Additionally, transmitting the data set may include data transmission over one or more of a wired connection or a wireless connection, where the wired connection may include one or more of a serial port connection, or a USB connection, and further, where the wireless connection may include one or more of an RF communication link, a BLUETOOTH® communication link, an infrared communication link, or a WI-FI™ communication link.

In one aspect, the data set may be transmitted within a predetermined time period from when the data associated with the monitored analyte level is acquired, where the predetermined time period may include one of less than 5 milliseconds, less than one second, or less than 5 minutes.

An apparatus in accordance with still yet another aspect may include a data storage unit, and a processing unit coupled to the data storage unit, the processing unit configured to acquire data associated with a monitored analyte level, determine a glucose level based at least in part on the acquired data associated with the monitored analyte level, and manipulate a data set based on a processing mode following the glucose level determination, where the processing mode includes one of a data set transmission and output display, a data set storing and output display without transmission, or a data set transmission and data set storing without output display.

The processing unit may be configured to automatically transmit the data set following the glucose level determination.

The data set may include one or more of the monitored analyte level, temperature information associated with the monitored analyte level, a data quality information associated with the monitored analyte level, or an error detection information associated with the monitored analyte level.

The data set may include one or more of a filtered glucose data, an unfiltered glucose data, glucose trend information, or glucose alarm condition determination.

In another aspect, the processing unit may be configured to transmit the data set over one or more of a wired connection or a wireless connection, where the wired connection may include one or more of a serial port connection, or a USB connection, and further, the wireless connection may include one or more of an RF communication link, a BLUETOOTH® communication link, an infrared communication link, or a WI-FI™ communication link.

The processing unit may be configured to transmit the data set within a predetermined time period from when the data associated with the monitored analyte level is acquired, where the predetermined time period may include one of less than 5 milliseconds, less than one second, or less than 5 minutes.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of determining a composite sensitivity for an analyte sensor of an electronic analyte monitoring system to compensate for an outlier or erroneous sensitivity, the method comprising:
   positioning an analyte sensor in fluid contact with bodily fluid in a human body;
   generating, with the analyte sensor, first data corresponding to a monitored analyte level in the bodily fluid;
   determining a new sensor sensitivity, using a processor, based on the generated first data when a first difference between a current sensor sensitivity and a prior sensor sensitivity is not within a predetermined range;
   determining, using the processor, if a second difference between the new sensor sensitivity and one of the current sensor sensitivity or the prior sensor sensitivity is within the predetermined range;
   after it is determined that the second difference between the new sensor sensitivity and one of the current sensor sensitivity or the prior sensor sensitivity is within the predetermined range, then determining, using the processor, a composite sensitivity based on the new sensor sensitivity and the one of the current sensor sensitivity or the prior sensor sensitivity that was used in determining that the second difference is within the predetermined range; and
   generating, using the processor, second data based on calibrating the first data using the composite sensitivity, the second data corresponding to a monitored analyte level.

2. The method of claim 1, including determining a calibration time period based on a predetermined calibration schedule.

3. The method of claim 2, wherein the predetermined calibration schedule includes a plurality of calibration time periods after positioning of the analyte sensor in fluid contact with the bodily fluid.

4. The method of claim 3, wherein the plurality of calibration time periods is determined based on a valid calibration procedure to calibrate the positioned analyte sensor.

5. The method of claim 1, further comprising generating a notification including a request for a reference measurement value.

6. The method of claim 5, wherein the request includes one or more of a text information, a graphical information, an audible information, or a combined one or more of the text, graphical or audible information to alert a user to enter the reference measurement value.

7. The method of claim 1, further including comparing the current sensor sensitivity to a nominal sensitivity for a first baseline calibration of the analyte sensor.

8. The method of claim 1, wherein the bodily fluid is interstitial fluid.

9. The method of claim 1, wherein the second difference determined to be within the predetermined range is between the new sensor sensitivity and the current sensor sensitivity, and wherein the composite sensitivity is based on the new sensor sensitivity and the current sensor sensitivity.

10. The method of claim 1, wherein the second difference determined to be within the predetermined range is between the new sensor sensitivity and the prior sensor sensitivity, and wherein the composite sensitivity is based on the new sensor sensitivity and the prior sensor sensitivity.

11. An electronic analyte monitoring system capable of determining a composite sensitivity for an analyte sensor to compensate for an outlier or erroneous sensitivity, the system comprising:
   an analyte sensor adapted to contact bodily fluid in a human's body and configured to generate first data corresponding to monitored analyte level in the bodily fluid;
   a data storage unit; and
   a processing unit operatively coupled to the data storage unit and the analyte sensor, and configured to:
      determine a new sensor sensitivity based on the generated first data from the analyte sensor when a first difference between a current sensor sensitivity and a prior sensor sensitivity is not within a predetermined range, determine if a second difference between the new sensor sensitivity and one of the current sensor sensitivity or the prior sensor sensitivity is within the predetermined range, after it is determined that the second difference between the new sensor sensitivity and one of the current sensor sensitivity or the prior sensor sensitivity is within the predetermined range, then determine a composite sensitivity based on the new sensor sensitivity and the one of the current sensor sensitivity or the prior sensor sensitivity that was used to determine that the second difference is within the predetermined range; and generate second data based on a calibration of the first data using the composite sensitivity, the second data corresponding to a monitored analyte level.

12. The system of claim 11, wherein the processing unit is configured to determine a calibration time period based on a predetermined calibration schedule.

13. The system of claim 12, wherein the predetermined calibration schedule includes a plurality of calibration time periods after positioning of the analyte sensor in fluid contact with the bodily fluid.

14. The system of claim 13, wherein the plurality of calibration time periods is determined based on a valid calibration procedure to calibrate the positioned analyte sensor.

15. The system of claim 11, further including an output unit operatively coupled to the processing unit, the output unit configured to generate and to output a notification to request for a reference measurement value.

16. The system of claim 15, wherein the request includes one or more of a text information, a graphical information, an audible information, or a combined one or more of the text, graphical or audible information.

17. The system of claim 15, wherein the processing unit is configured to store the generated notification in the data storage unit.

18. The system of claim 11, wherein the processing unit is further configured to compare the current sensor sensitivity to a nominal sensitivity for a first baseline calibration of the analyte sensor.

19. The system apparatus of claim 11, wherein the bodily fluid is interstitial fluid.

20. The system of claim 11, wherein the second difference determined to be within the predetermined range is between the new sensor sensitivity and the current sensor sensitivity, and wherein the composite sensitivity is based on the new sensor sensitivity and the current sensor sensitivity.

21. The system of claim 11, wherein the second difference determined to be within the predetermined range is between the new sensor sensitivity and the prior sensor sensitivity, and wherein the composite sensitivity is based on the new sensor sensitivity and the prior sensor sensitivity.

* * * * *